US012667723B2

(12) United States Patent
Nemechek

(10) Patent No.: US 12,667,723 B2
(45) Date of Patent: Jun. 30, 2026

(54) SYSTEMS AND METHODS FOR TREATING AUTISM SPECTRUM DISORDER, DEVELOPMENTAL DISORDERS AND OTHER MEDICAL CONDITIONS

(71) Applicant: Patrick M. Nemechek, Buckeye, AZ (US)

(72) Inventor: Patrick M. Nemechek, Buckeye, AZ (US)

( * ) Notice: Subject to any disclaimer, the term of this patent is extended or adjusted under 35 U.S.C. 154(b) by 367 days.

(21) Appl. No.: 18/132,301

(22) Filed: Apr. 7, 2023

(65) Prior Publication Data

US 2023/0321437 A1      Oct. 12, 2023

Related U.S. Application Data

(60) Provisional application No. 63/329,190, filed on Apr. 8, 2022.

(51) Int. Cl.
| | |
|---|---|
| *A61N 1/04* | (2006.01) |
| *A61N 1/36* | (2006.01) |
| *A61N 1/378* | (2006.01) |

(52) U.S. Cl.
CPC ....... *A61N 1/36025* (2013.01); *A61N 1/0484* (2013.01); *A61N 1/3787* (2013.01)

(58) Field of Classification Search
CPC .......................... A61N 1/36025; A61N 1/0456
See application file for complete search history.

(56) References Cited

U.S. PATENT DOCUMENTS

| | | | |
|---|---|---|---|
| 5,458,625 | A | 10/1995 | Kendal |
| 6,205,359 | B1 | 3/2001 | Boveja |
| 7,706,875 | B2 | 4/2010 | Buras et al. |
| 7,797,042 | B2 | 9/2010 | Dietrich et al. |
| 7,885,709 | B2 | 2/2011 | Ben-David |
| 8,755,892 | B2 | 6/2014 | Amurthur et al. |
| 8,843,210 | B2 | 9/2014 | Simon et al. |
| 8,874,205 | B2 | 10/2014 | Simon et al. |
| 8,918,178 | B2 | 12/2014 | Simon et al. |
| 9,662,490 | B2 | 5/2017 | Tracey et al. |
| 10,130,809 | B2 | 11/2018 | Cartledge et al. |
| 10,166,395 | B2 | 1/2019 | Tracey et al. |
| 10,335,396 | B2 | 7/2019 | Nemechek |
| 10,363,419 | B2 | 7/2019 | Simon et al. |
| 10,639,468 | B2 | 5/2020 | Cook et al. |
| 10,661,048 | B1 | 5/2020 | Hill et al. |
| 10,933,240 | B2 | 3/2021 | Kressel et al. |
| 11,083,892 | B2 | 8/2021 | Terrando et al. |

(Continued)

FOREIGN PATENT DOCUMENTS

| | | |
|---|---|---|
| CN | 201710816 U | 1/2011 |
| CN | 108348517 B | 11/2021 |

(Continued)

OTHER PUBLICATIONS

US 10,238,859 B2, 03/2019, Simon et al. (withdrawn)

(Continued)

*Primary Examiner* — Alyssa M Alter
(74) *Attorney, Agent, or Firm* — PROCOPIO, CORY, HARGREAVES & SAVITCH LLP

(57) ABSTRACT

Provided herein are methods for treating autism; and systems and devices for administering transcutaneous auricular vagal nerve stimulation (taVNS).

8 Claims, 15 Drawing Sheets

Earclip 1305
Electrical Contact 1310
Electrical Contact 1320
Elongated Member 1340
1350 Elongated Member
1330 Hinge

(56) References Cited

U.S. PATENT DOCUMENTS

| | | | |
|---|---|---|---|
| 11,116,978 | B2 | 9/2021 | Craig |
| 11,123,560 | B1 | 9/2021 | Nemechek |
| 11,173,307 | B2 | 11/2021 | Levine et al. |
| 11,191,953 | B2 | 12/2021 | Simon et al. |
| 2005/0075702 | A1 | 4/2005 | Shafer |
| 2005/0154425 | A1 | 7/2005 | Boveja et al. |
| 2006/0122675 | A1 | 6/2006 | Libbus et al. |
| 2006/0178703 | A1 | 8/2006 | Huston et al. |
| 2007/0150027 | A1 | 6/2007 | Rogers |
| 2007/0250145 | A1 | 10/2007 | Kraus et al. |
| 2008/0051852 | A1 | 2/2008 | Dietrich et al. |
| 2008/0140138 | A1 | 6/2008 | Ivanova et al. |
| 2008/0249439 | A1 | 10/2008 | Tracey et al. |
| 2008/0249594 | A1 | 10/2008 | Dietrich et al. |
| 2016/0038559 | A1 | 2/2016 | Palmer et al. |
| 2017/0087364 | A1 | 3/2017 | Cartledge et al. |
| 2017/0246481 | A1 | 8/2017 | Mishelevich |
| 2017/0368329 | A1* | 12/2017 | Tyler ....................... G10L 15/02 |
| 2018/0271869 | A1 | 9/2018 | Liu et al. |
| 2018/0339148 | A1* | 11/2018 | Kong ................. A61N 1/36025 |
| 2019/0201707 | A1 | 7/2019 | Stubbeman |
| 2020/0188671 | A1 | 6/2020 | Lovett |
| 2020/0368527 | A1 | 11/2020 | Asirvatham |
| 2021/0052896 | A1 | 2/2021 | Howard |
| 2021/0137909 | A1 | 5/2021 | Neil et al. |
| 2021/0220365 | A1 | 7/2021 | Shapiro et al. |
| 2021/0252279 | A1 | 8/2021 | Kong |
| 2021/0316141 | A1 | 10/2021 | Rennaker, II et al. |

FOREIGN PATENT DOCUMENTS

| | | |
|---|---|---|
| CN | 113577564 A | 11/2021 |
| KR | 1020210136627 A | 11/2021 |
| WO | 2012156052 A2 | 11/2012 |
| WO | 2012168543 A1 | 12/2012 |
| WO | 2016015802 A1 | 2/2016 |
| WO | 2020176276 A1 | 9/2020 |
| WO | 2020198453 A1 | 10/2020 |
| WO | 2020252428 A1 | 12/2020 |
| WO | 2021051152 A1 | 3/2021 |
| WO | 2021236977 A1 | 11/2021 |

OTHER PUBLICATIONS

Das, "Can Vagus Nerve Stimulation Halt or Ameliorate Rheumatoid Arthritis and Lupus?", Lipids in Health and Disease; Jan. 2011, 7 pages.

Kim et al., "Brain Stimulation and Modulation for Autism Spectrum Disorder", Hanyang Medical Reviews • 36:65-71; Jan. 2016, 8 pages.

Pavlov et al., "Neural Circuitry and Immunity", HHS Public Access, Immunol Res. Dec. 2015 ; 63(0): 38-57, 33 pages.

Jin et al., "Transcutaneous Vagus Nerve Stimulation: A Promising Method for Treatment of Autism Spectrum Disorders", Frontiers in Neuroscience, Jan. 2017 | vol. 10 | Article 609, 7 pages.

Engineer et al., "Vagus Nerve Stimulation as a Potential Adjuvant to Behavioral Therapy for Autism and Other Neurodevelopmental Disorders", Journal of Neurodevelopmental Disorders, Article No. 20, Jul. 4, 2017, 8 pages.

Derakhshan, "Vagal Nerve Stimulation for the Treatment of Autism", Department of Neurosurgery, Neuroscience Research Center, Mental Illness 2015; vol. 7:5788.

Levy et al., "Vagus Nerve Stimulation Therapy in Patients With Autism Spectrum Disorder and Intractable Epilepsy: Results From the Vagus Nerve Stimulation Therapy Patient Outcome Registry".

D Park, "The Effects of Vagus Nerve Stimulation Therapy on Patients With Intractable Seizures and Either Landau-Kleffner Syndrome or Autism" Department of Neurology (child), Medical College of Georgia, vol. 4, Issue 3, Jun. 2003, pp. 286-290.

Van Horn et al., "Neuromodulation of Autism Spectrum Disorders Using Vagal Nerve Stimulation", Clin Neurosci. May 2019:63:8-12. doi: 10.1016/j.jocn.2019.01.042. Epub Feb. 4, 2019.

Hull et al., "Autistic spectrum disorder, epilepsy, and vagus nerve stimulation", NIH, Childs Nerv Syst Aug. 2015;31(8):1377-85. doi: 10.1007/s00381-015-2720-8. Epub Apr. 29, 2015.

C Warwick et al., "Effects of Vagus Nerve Stimulation in a Patient With Temporal Lobe Epilepsy and Asperger Syndrome: Case Report and Review of the Literature". Mar. 2007.

Engineer, "Enhancing Speech Processing in a Rat Model of Autism Using Vagus Nerve Stimulation", National Institute of Health (NIH), 2018.

Tsimerinov et al., "Does Vagus Nerve Stimulation effect behavior in Autistic Patients with Intractable Epilepsy?", American Epilepsy Society, "2011.

Engineer et al, Vagus Nerve Stimulation Paired with Sounds Improves Auditory Processing in Rat Models of Neurodevelopmental Disorders:. Brain Stimulation 14, 2021; 1708-1752.

Danielson, "Student wins innovation prize with brain stimulation device" http://academicdepartments.musc.edu/catalyst/archives/2015/2-6Innovation.html, 4 pages, 2015.

Transcutaneous Vagus Nerve Stimulation; Parasym Health, Anxiety Disorder Treatment; http://www.parasym.co/anxiety-treatment.html, Aug. 2, 2017, 5 pages.

Bunting, "Tickling your ear could be good for your heart", University of Leeds | News > Health, Aug. 20, 2014, 5 pages.

White Ear Clip Electrodes for Electrotherapy Stimulation; TENSPros.com, Aug. 2, 2017, 5 pages.

* cited by examiner

Figures 3, 4:
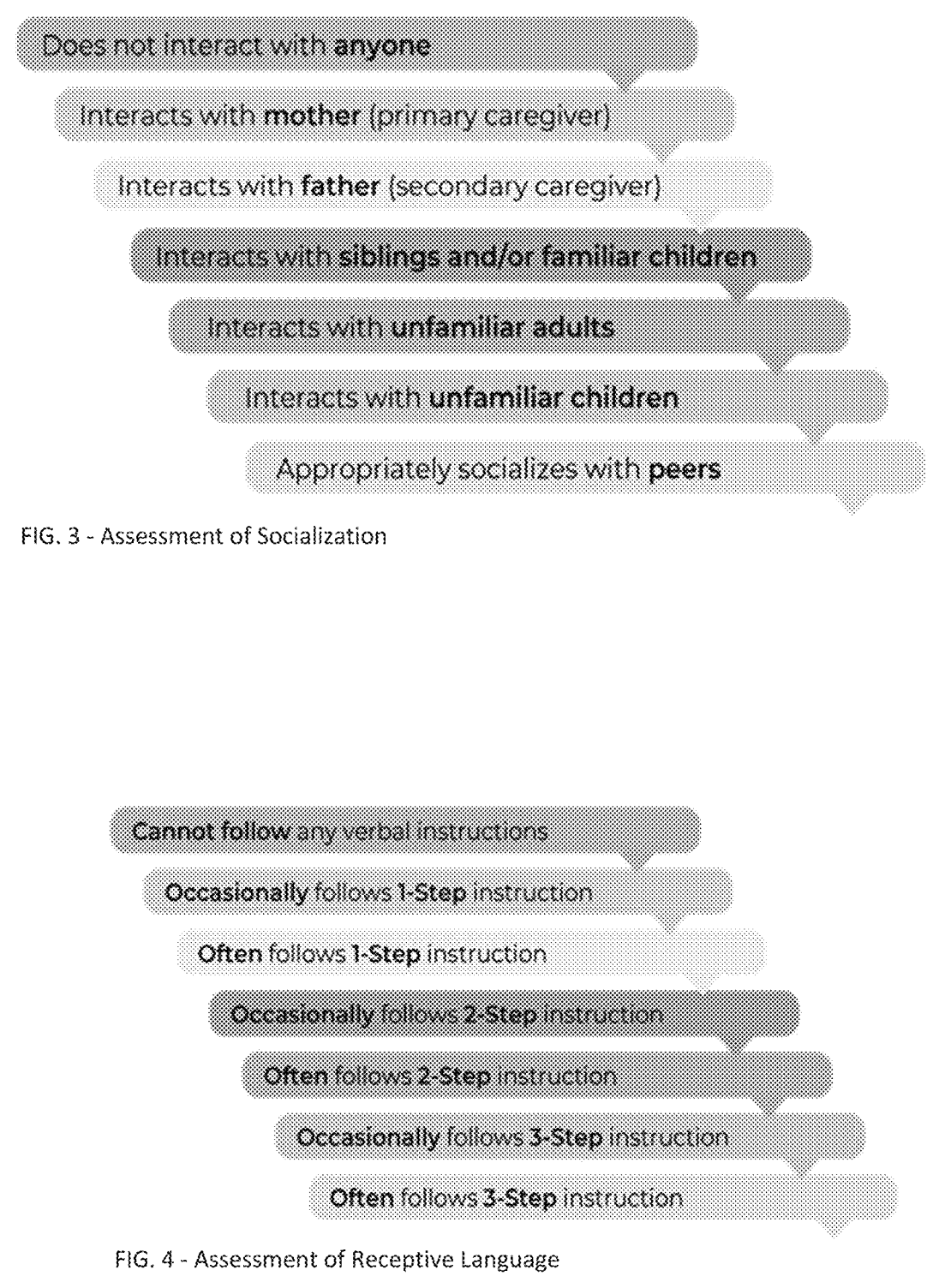

Does not interact with anyone

Interacts with mother (primary caregiver)

Interacts with father (secondary caregiver)

Interacts with siblings and/or familiar children

Interacts with unfamiliar adults

Interacts with unfamiliar children

Appropriately socializes with peers

FIG. 3 - Assessment of Socialization

Cannot follow any verbal instructions

Occasionally follows 1-Step instruction

Often follows 1-Step instruction

Occasionally follows 2-Step instruction

Often follows 2-Step instruction

Occasionally follows 3-Step instruction

Often follows 3-Step instruction

FIG. 4 - Assessment of Receptive Language

Figures 5, 6:
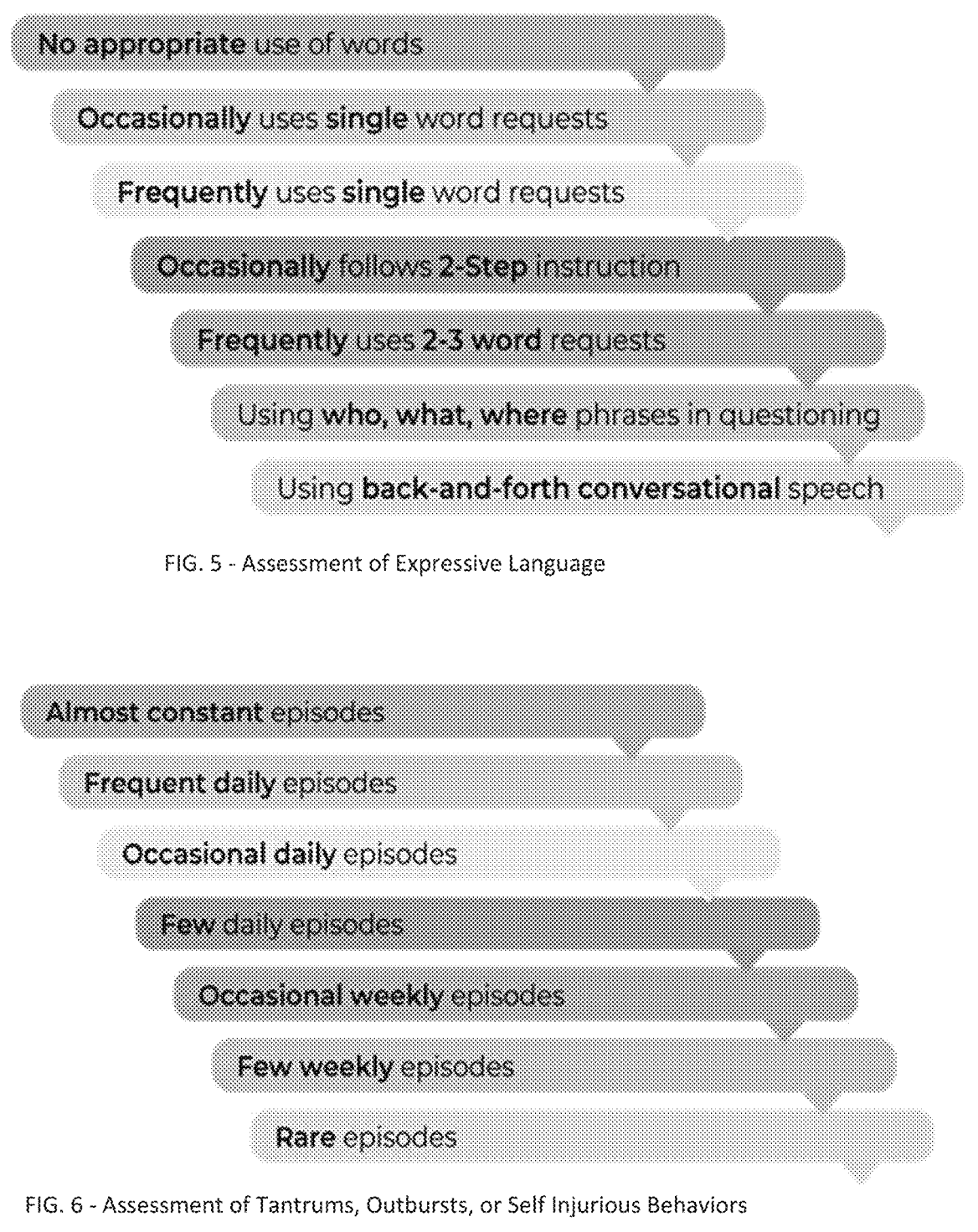

No appropriate use of words

Occasionally uses single word requests

Frequently uses single word requests

Occasionally follows 2-Step instruction

Frequently uses 2-3 word requests

Using who, what, where phrases in questioning

Using back-and-forth conversational speech

FIG. 5 - Assessment of Expressive Language

Almost constant episodes

Frequent daily episodes

Occasional daily episodes

Few daily episodes

Occasional weekly episodes

Few weekly episodes

Rare episodes

FIG. 6 - Assessment of Tantrums, Outbursts, or Self Injurious Behaviors

Figures 7, 8:
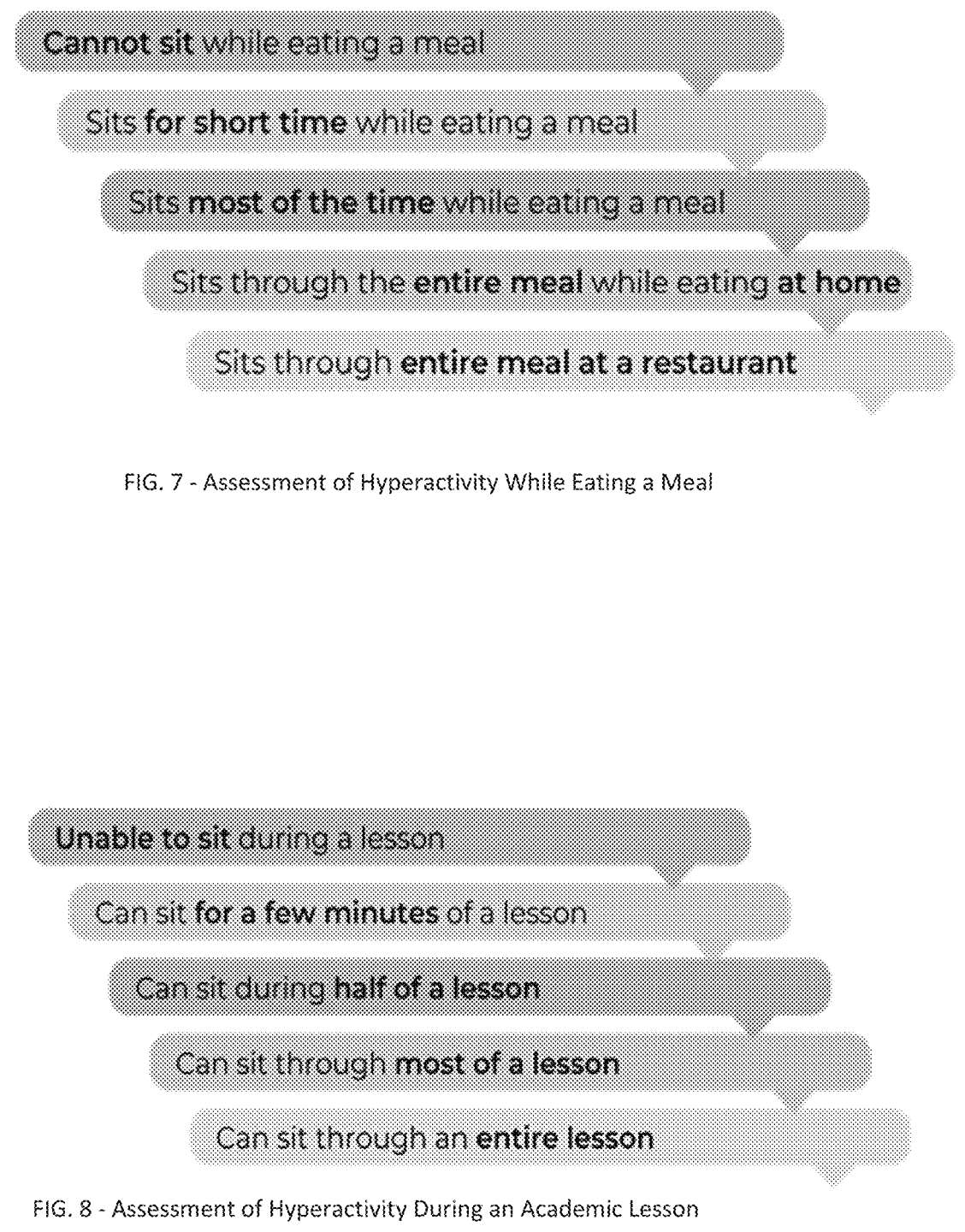

Cannot sit while eating a meal

Sits for short time while eating a meal

Sits most of the time while eating a meal

Sits through the entire meal while eating at home

Sits through entire meal at a restaurant

FIG. 7 - Assessment of Hyperactivity While Eating a Meal

Unable to sit during a lesson

Can sit for a few minutes of a lesson

Can sit during half of a lesson

Can sit through most of a lesson

Can sit through an entire lesson

FIG. 8 - Assessment of Hyperactivity During an Academic Lesson

Main Processor
& Bluetooth
910

TransmissionModule
920

Power Button

2φ Screw Hole *2

BT_Q9

BUZZER

Uint Status
Indicators(2+2)

Type C Female
(BAT Charge and
HV Output)

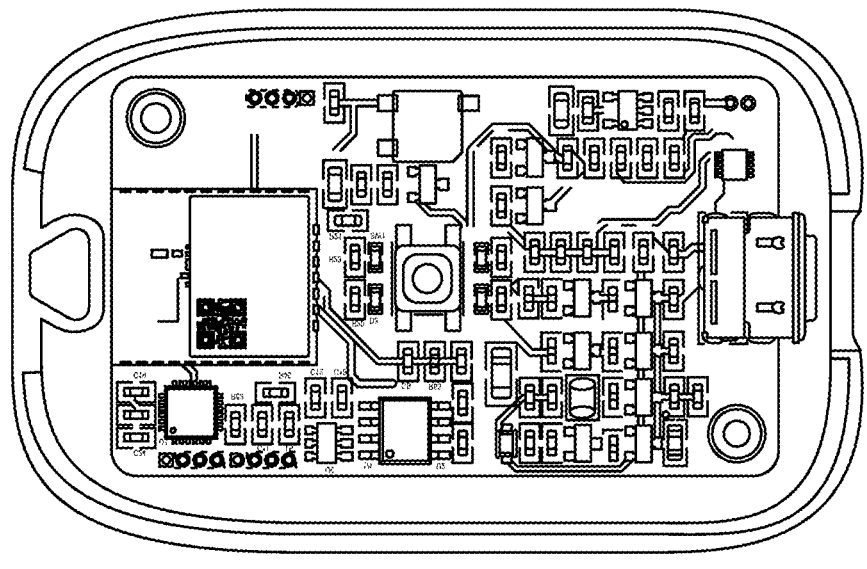
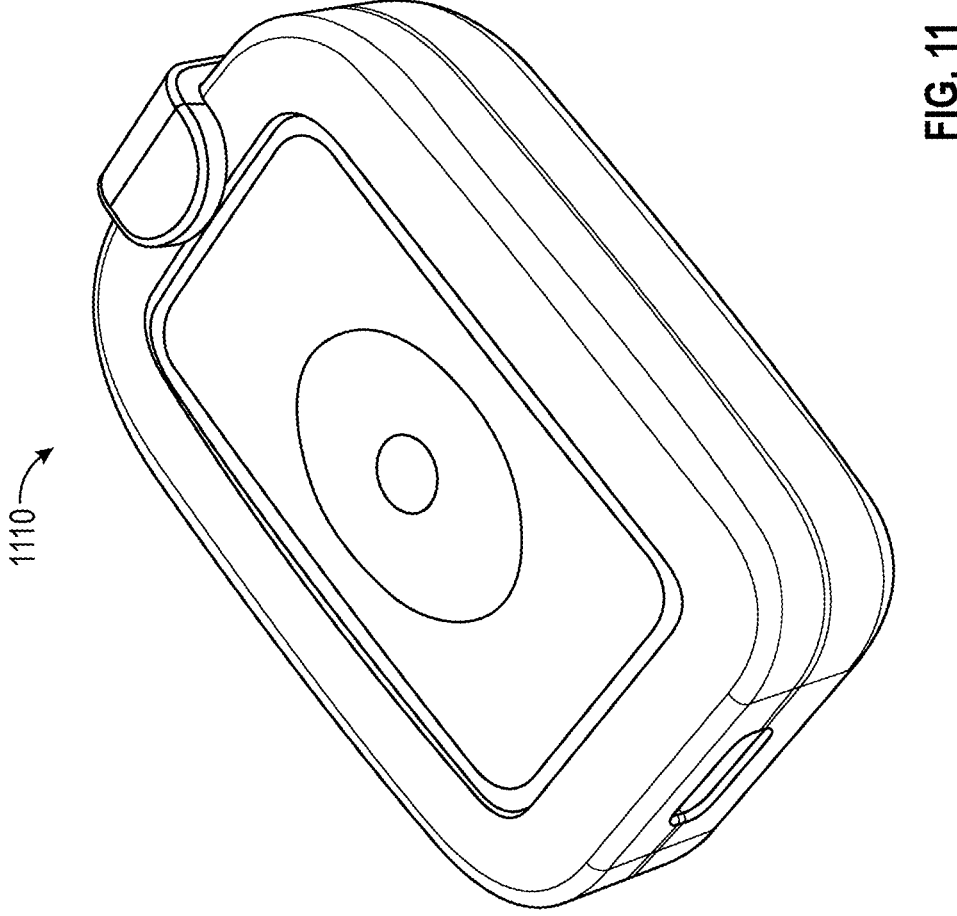
FIG. 11
1110

1510
Tragus

1505
Earclip

1520
Concha

1505
Earclip

Connector
1610

1605
Earclip

1620
Wired Dongle

Earclip
1605

1630
Port

1640
Central Axis

1610
Connector

1610
Connector

| Classification | Electrically conductive | | |
|---|---|---|---|
| Grade | KE-3601SB-U | KE-3711-U | KE-3801M-U |
| Appearance | | Black | |
| Density  23°C            g/cm³ | 1.17 | 1.14 | 1.20 |
| Williams plasticity (10 min after remix) | 450 | 480 | 630 |
| Curing agent — Curing agent name | C-8A | C-8A | HC-101/CAT-PL-2 |
| Curing agent — Standard addition quantity*1 | 1.0 | 1.0 | 2.7/0.1 |
| Linear shrinkage*2            % | 4.2 | — | — |
| Physical strength — Hardness  Durometer A | 62 | 66 | 73 |
| Physical strength — Tensile strength    MPa | 7.0 | 6.5 | 5.3 |
| Physical strength — Elongation at break  % | 290 | 170 | 190 |
| Physical strength — Tear strength crescent piece    kN/m | 10 | — | 15*6 |
| Compression set  180°C x 22  h | — | 12 | 18*7 |
| Dielectric breakdown strength  Normal state    kV | — | — | — |
| Volume resistivity Normal state    TΩ·m | 0.05*8 | 0.05*8 | 0.03*8 |

FIGURE 18

SYSTEMS AND METHODS FOR TREATING AUTISM SPECTRUM DISORDER, DEVELOPMENTAL DISORDERS AND OTHER MEDICAL CONDITIONS

CROSS-REFERENCE TO RELATED APPLICATIONS

This Application claims the benefit of priority under 35 USC 119(e) based on U.S. Provisional Application No. 63/329,190, Filed on Apr. 8, 2022, the contents of which is incorporated by reference herein.

TECHNICAL FIELD

The invention relates to methods for increasing recovery from autism and other neurological, musculoskeletal, metabolic, and genetic disorders that arise during childhood.

INTRODUCTION

The United States has been experiencing a steady incline in the prevalence of children affected with autism over the last 30 years, with prevalence estimates as recent as 2016 indicating that 1 in 54 children are affected by autism spectrum disorder. For children between 3 and 17 years of age, this means there are over 1.7 million children with autism within the US. The number of children with developmental disorders not specified as autism is believed to be 2-3 times the number as children with autism.

Over the last 30 years, therapy for these conditions has not significantly advanced and is limited to behavior modification, speech therapy, occupational therapy, physical therapy and the use of pharmaceutical agents to control hyperactivity, aggression, anxiety, and co-existing attention disorders.

Recent scientific advances are highlighting that chronic inflammation within the central nervous system is involved in autism and a variety of other childhood as well as adult neurological disorders. A variety of approaches to control chronic neuroinflammation in adults has been evolving and one such proposed therapeutic approach is the use of vagus nerve stimulation to improve the immune system's ability to more properly regulate the body's inflammatory response.

The vagus nerve is a neurological conduit that carries bidirectional signals between the parasympathetic branch of the autonomic nervous system and the organs of the body including the immune system. Electrical stimulation of the vagus nerve is presently used for the treatment of epilepsy and depression by means of a surgically implanted VNS device.

Additional research has discovered a branch of the vagus nerve that extends to the ear (auricular branch of the vagus nerve; ABVN) and is located within the region of the tragus, concha and cymba conchae. When transcutaneous vagus nerve stimulation is applied at the ear (taVNS), the same regions of the autonomic nervous system are stimulated as when the vagus nerve is stimulated with the surgically implanted vagus nerve stimulator.

One major effect of vagus nerve stimulation is improved regulation of the immune system's inflammatory response, which makes taVNS capable of reducing excessive inflammatory reactions within the body. Studies have demonstrated the ability of taVNS to improve inflammatory conditions such as rheumatoid arthritis, inflammatory bowel disease and the cytokine storm associated with COVID-19 infection.

Chronic inflammation within the central nervous system can lead to impairment of the brain's natural ability to efficiently prune, repair and rejuvenate itself. When chronic neuroinflammation occurs during childhood, impairment of these critical functions leads to a wide variety of developmental, motor and sensory disorders commonly associated with autism as well pervasive developmental disorders.

Another major effect of vagus nerve stimulation is to improve production, clearance and function of the brain's natural repair mechanisms including microglia, neurotrophins, chemoreceptor system, stem cells, neurogenesis, apoptosis, and regeneration.

Another major effect of vagus nerve stimulation is improved functionality of the central nervous system including the parasympathetic and sympathetic branches of the autonomic nervous system, limbic system, enteric nervous system, peripheral nervous system, and somatic motor system.

Another major effect of vagus nerve stimulation is improved function of organs and organ function, the vagus nerve, hormone regulation, immune system regulation, peripheral nerves, tissue repair, and emotional regulation.

Another major effect of vagus nerve stimulation is improvement in attention, awareness, eye contact, constipation, potty training, reading competency, mathematical competency, learning, intellect, comprehension, memory recall, emotional regulation, anxiety, aggression, self-injurious behavior, violent behavior, impulse control, hyperactivity, dietary preferences, and socialization.

Another major effect of vagus nerve stimulation is alteration of the gut microbiome, de-activation of disease-causing genes, improvement of mitochondrial function, improvement of endoplasmic reticulum function, improved regulation of cerebral spinal fluid production and improvement in lymphatic flow.

Accordingly, there is a need in the art for improving inflammation control within children with autism spectrum disorder and other developmental medical conditions.

SUMMARY

Provided herein are methods for preventing, treating, or preventing recurrence of symptoms of autism or autism spectrum disorder in a subject in need thereof, said method comprising: administering to said subject an effective amount of electrical vagus nerve stimulation (VNS). In certain embodiments, the subject exhibits inflammation or gut microbiome dysfunction. In further embodiments, the subject is refractory to standard autism treatments. In particular embodiments, the subject is a child.

Also provided herein are methods for preventing, reducing or reversing chronic inflammation in children with autism, developmental abnormalities and other medical conditions comprising administering to said subject an effective amount of electrical vagus nerve stimulation (VNS). Also provided herein are methods for treating refractory symptoms or preventing return of symptoms in children with autism, developmental abnormalities and other medical conditions comprising administering to said subject an effective amount of electrical vagus nerve stimulation (VNS). In some embodiments, chronic inflammation is caused by a conditions selected from or related to recurrent or reactivated infections with a virus, bacteria, archaebacteria, spirochete, helminth, fungi or parasite; immune system abnormality; impairment of immune system regulatory factors; autonomic nervous system dysfunction; vagus nerve damage or dysfunction; an autoimmune disorder; disturbances of intestinal microbiome; bacterial translocation; disturbances of intestine permeability; dietary factors; omega fatty acid imbalances; environmental pollutants; and/or any substance that is foreign to the body.

In certain embodiments, the electrical vagal nerve stimulation for preventing, reducing or reversing chronic inflammation has physiological effects including improve production, clearance and function of the brain's natural repair mechanisms including microglia, neurotrophins, chemoreceptor system, stem cells, neurogenesis, apoptosis, and regeneration. In particular embodiments, the vagal nerve stimulation for preventing, reducing or reversing chronic inflammation has physiological effects including improved functionality of the central nervous system including the parasympathetic and sympathetic branches of the autonomic nervous system, limbic system, enteric nervous system, peripheral nervous system, and somatic motor system. In certain embodiments, the vagal nerve stimulation for preventing, reducing or reversing chronic inflammation has physiological effects including improved function of organs and organ function, the vagus nerve, hormone regulation, immune system regulation, peripheral nerves, tissue repair, and emotional regulation. In particular embodiments, the vagal nerve stimulation for preventing, reducing or reversing chronic inflammation has physiological effects including alteration of the gut microbiome, de-activation of disease-causing genes, improvement of mitochondrial function, improvement of endoplasmic reticulum function, improved regulation of cerebral spinal fluid production and improvement in lymphatic flow. In particular embodiments, the vagal nerve stimulation for preventing, reducing or reversing chronic inflammation has physiological effects including improvement in attention, awareness, eye contact, constipation, potty training, reading competency, mathematical competency, learning, intellect, comprehension, memory recall, emotional regulation, anxiety, aggression, self-injurious behavior, violent behavior, impulse control, hyperactivity, dietary preferences, and socialization. In embodiments, these physiological effects result from methods of treating or preventing the conditions causing chronic inflammation described above, thereby treating or preventing said conditions in subjects in need thereof.

In particular embodiments, the VNS can be provided transcutaneously using electrical stimulation through an electrical current. In one embodiment, the electrical stimulation is achieved by clipping electrodes across the tragus or concha of an ear and inducing an electrical current with a transcutaneous electrical nerve stimulation (TENS) unit. In particular embodiments, the electrical current has a frequency in the range selected from the group consisting of: about 0.1 Hz to about 30 Hz, about 0.3 Hz to about 25 Hz, about 0.5 Hz to about 20 Hz, about 0.7 Hz to about 15 Hz, about 0.9 Hz to about 10 Hz, about 1.0 Hz to about 9 Hz, about 1.2 Hz to about 8 Hz, about 1.4 Hz to about 7 Hz, about 1.6 Hz to about 6 Hz, or 2 Hz to about 5 Hz. In particular embodiments, the electrical current has a pulse width in the range selected from: about 20 to about 1000 μs, about 30 to about 900 μs, about 40 to about 800 μs, about 50 to about 700 μs, about 60 to about 600 μs, about 70 to about 500 μs, about 80 to about 450 μs, about 90 to about 400 μs, about 100 to about 350 μs, about 110 to about 325 μs, about 120 to about 300 μs, about 130 to about 275 μs, about 140 to about 260 μs, and about 150 to about 250 μs. In certain embodiments, the electrical current is in a range selected from: about 0.1 to about 5.0, about 0.2 to about 4.0, about 0.3 to about 3.0, about 0.4 to about 2.0, about 0.5 to about 1.0 mAmps or increased to a level that is perceived and tolerated by the user. In a particular embodiment of the invention, the electrical current has a frequency at 2-5 Hz, pulse width at 150-250 μs and 0.5-1.0 mAmps.

In certain embodiments, the electrical stimulation doses can range about 30 sec to about 5 min; from about 45 sec to about 4.5 mins; about 1 min to about 4 min; about 1.5 to about 3.5 min; about 2 min to about 3 min; about 30 sec to about 5 min; from about 30 sec to about 4.5 mins; about 30 sec to about 4 min; about 30 sec to about 3.5 min; about 30 sec to about 3 min; about 30 sec to about 2.5 min; about 30 sec to about 2 min; about 30 sec. to about 1.5 min; or about 30 sec to about 1 min. In other embodiments, VNS can be applied up to 24 hours per day. The number of doses or treatments per day can be selected from the group consisting of 1, 2, 3, 4, 5, 6, 7, 8, 9, 10, 11, 12, 13, 14, 15, 16, 17, 18, 19, and 20. In other embodiments the number of doses or treatments can range from 1-100 per day.

The length of treatment can be from 1 to 120 months, 1 to 96 months, 1 to 72 months, 1 to 48 months, 1 to 24 months, 1 to 12 months. In a particular embodiment, the treatment is performed until the symptoms of subject receiving the treatment resolve; such treatment can be for months or years, up to and including the lifetime of the subject. In a particular embodiment, the treatment is performed to prevent inflammation, to prevent a condition described above, or to prevent the recurrence of symptoms for any number of days, months, or years, up to and including the lifetime of the patient. In another embodiment, the subject receives 1-2, 5-minute treatments per day for 48 months.

Accordingly, provided herein are the following items:

1. A method for preventing, treating, or preventing recurrence of symptoms of autism or autism spectrum disorder in a subject in need thereof, said method comprising:
   administering to said subject an effective amount of electrical vagus nerve stimulation (VNS).
2. The method of item 1, wherein the subject exhibits inflammation or gut microbiome dysfunction.
3. The method of item 1, wherein the subject is refractory to standard autism treatments.
4. The method of item 1, wherein the VNS is provided transcutaneously using electrical stimulation through an electrical current.
5. The method of item 4, wherein the electrical stimulation is achieved by providing opposing electrodes across the tragus or concha of an ear and inducing an electrical current with a transcutaneous electrical nerve stimulation (TENS) unit.
6. The method of item 4, wherein the electrical current has a frequency in the range selected from the group consisting of: about 0.1 Hz to about 30 Hz, about 0.3 Hz to about 25 Hz, about 0.5 Hz to about 20 Hz, about 0.7 Hz to about 15 Hz, about 0.9 Hz to about 10 Hz, about 1.0 Hz to about 9 Hz, about 1.2 Hz to about 8 Hz, about 1.4 Hz to about 7 Hz, about 1.6 Hz to about 6 Hz, or about 2 Hz to about 5 Hz; has a pulse width in the range selected from: about 20 to about 1000 us about 30 to about 900 μs, about 40 to about 800 μs, about 50 to about 700 μs, about 60 to about 600 μs, about 70 to about 500 μs, about 80 to about 450 μs, about 90 to about 400 μs, about 100 to about 350 μs, about 110 to about 325 μs, about 120 to about 300 μs, about 130 to about 275 μs, about 140 to about 260 μs, and about 150 to about 250 μs.
7. The method of item 4, wherein the electrical current is in a range selected from: about 0.1 to about 5.0, about 0.2 to about 4.0, about 0.3 to about 3.0, about 0.4 to about 2.0, or about 0.5 to about 1.0 mAmps.

8. The method of item 4, wherein the electrical current has a frequency at 2-5 Hz, pulse width at 150-250 µs and 0.5-1.0 mAmps.

9. The method of item 4, wherein the electrical stimulation is performed for about 30 sec to about 10 min; about 2 min to about 8 min; about 4 min to about 6 min; or about 5 min.

10. The method of item 9, wherein the number of doses per day is selected from the group consisting of 1, 2, 3, 4, 5, 6, 7, 8, 9, 10, 11, 12, 13, 14, 15, 16, 17, 18, 19, 20.

11. The method of item 9, wherein the length of treatment is 1 to 120 months, 1 to 96 months, 1 to 72 months, 1 to 48 months, 1 to 24 months, or 1 to 12 months.

12. The method of item 9, wherein the subject receives 1-2, 5-minute treatments per day for 48 months.

13. A system for transcutaneous auricular vagal nerve stimulation (taVNS), comprising:
an earclip that, when attached to an ear, provides two electrical contacts on opposite sides of the ear;
a powersource that is electrically connected to the earclip and comprises at least one processor configured to provide configurable electrical pulses via the two electrical contacts, and a wireless communication device configured to communicate with a wireless device and the at least one processor, wherein the wireless communication device is configured to receive, from the wireless device, configuration information for configuring the configurable electrical pulses and to provide the configuration information to the at least one processor; and the wireless device, wherein the wireless device is configured to execute an application used to specify the configuration information and is further configured to provide the configuration information to the wireless communication device of the powersource.

14. The system of item 13, wherein powersource is electrically connected to the earclip via an electrical wire.

15. The system of item 13, wherein the earclip provides the two electrical contacts on the opposite sides of the ear lobe with pressure sufficient to maintain contact between each of the two electrical contacts and the ear lobe.

16. The system of item 13, wherein the configuration information comprises one or more of a duration associated with providing the configurable electrical pulses, a voltage associated with each of the configurable electrical pulses, a frequency of the configurable electrical pulses, and a pulse width of each of the configurable electrical pulses.

17. The system of item 14, wherein the electrical wire is less than 24, 23, 22, 21 20, 19, 18, 17, 16, 15, 14, 13, 12, 11, 10, 9, 8, 7, 6, 5, 4, 3, 2 inches in length.

18. The system of item 13, wherein the configurable electrical pulses are configured to provide afferent electrical stimulation.

19. The system of item 18 wherein the configurable electrical pulses are configured to be provided continuously for a configured duration at a configured frequency.

20. The system of item 18, wherein the system does not provide efferent electrical stimulation.

21. The system of item 13, wherein the wireless device is configured to communicate with the wireless communication device via Bluetooth.

22. The system of item 13, wherein the powersource is associated with a unique identifier.

23. The system of item 22, wherein the unique identifier permits activation or deactivation of the powersource.

24. The system of item 23, wherein the powersource further comprises a monitoring component configured to determine whether the earclip is connected to a user while providing the configurable electrical pulses, wherein the wireless communication device is further configured to transmit monitoring information regarding whether the earclip is connected to the user to the wireless device.

25. The system of item 24, wherein the wireless device is configured to provide, based on the monitoring information, additional monitoring information to a remote monitoring system, wherein the additional monitoring information comprises first configuration information associated with a set of configurable electrical pulses provided by the system and whether the earclip was connected to the user while providing the set of configurable electrical pulses.

26. The system of item 25, wherein the wireless device is further configured to receive activation information from the remote monitoring system, wherein the activation information comprises one of a first indication for the system to provide a first additional set of configurable electrical pulses or a second indication to stop providing a second additional set of configurable electrical pulses.

27. The system of item 13, wherein the powersource further comprises a rechargeable power source.

28. The system of item 13, wherein the earclip, when attached to the ear in a first configuration, provides the two electrical contacts on opposite of a tragus of the ear, and
wherein the earclip, when attached to the ear in a second configuration, provides the two electrical contacts on opposite of a concha of the ear.

29. A powersource of a transcutaneous vagus nerve stimulation (taVNS) system that is electrically connected to an earclip of the taVNS, comprising:
a memory;
a wireless communication device;
an energy source; and
at least one processor coupled to the memory and, based at least in part on information stored in the memory, the at least one processor is configured to:
receive, via the wireless communication device and from a wireless device of the taVNS system, configuration information for configuring the provision of adjustable electrical pulses; and
provide, based on the configuration information, the adjustable electrical pulses via the earclip.

30. An earclip for taVNS, comprising a first electrical contact on a first elongated member and a second electrical contact on a second elongated member forming a pair of electrical contacts opposite each other; a central axis of the first and second elongated member forming a hinge under torsional-pressure, with pressure sufficient to maintain contact between each of the first and second electrical contacts and an ear lobe; a port within each elongated member to receive electricity.

31. The earclip of item 30, wherein the electrical contacts are electrodes.

32. The earclip of item 30, wherein the torsional-pressure is applied via a spring.

33. The earclip of item 31, wherein the electrodes are made of an electrically conductive silicone rubber compound.

34. The earclip of item 30, wherein wherein the electricity is received via TENS cables or a wired dongle.

35. A method for preventing, treating, or preventing recurrence of symptoms of autism or autism spectrum disorder in a subject in need thereof, said method comprising:

administering to said subject an effective amount of electrical vagus nerve stimulation (VNS), wherein the VNS is provided by the system for transcutaneous auricular vagal nerve stimulation (taVNS) of item 13.

BRIEF DESCRIPTION OF THE DRAWINGS

FIG. 3 shows Assessment of Socialization

FIG. 4 shows Assessment of Receptive Language

FIG. 5 shows Assessment of Expressive Language

FIG. 6 shows Assessment of Tantrums, Outbursts, or Self Injurious Behaviors

FIG. 7 shows Assessment of Hyperactivity While Eating a Meal

FIG. 8 shows Assessment of Hyperactivity During an Academic Lesson

FIG. 11 shows additional views of a housing for the power source of the taVNS system and how the components shown in FIGS. 9 and 10 may be arranged in the housing in accordance with some aspects of the disclosure.

FIG. 18 shows the general physical properties of exemplary suitable silicone rubber compounds for use in making the soft electrical contacts of an earclip for providing taVNS.

DETAILED DESCRIPTION

Figure 1:
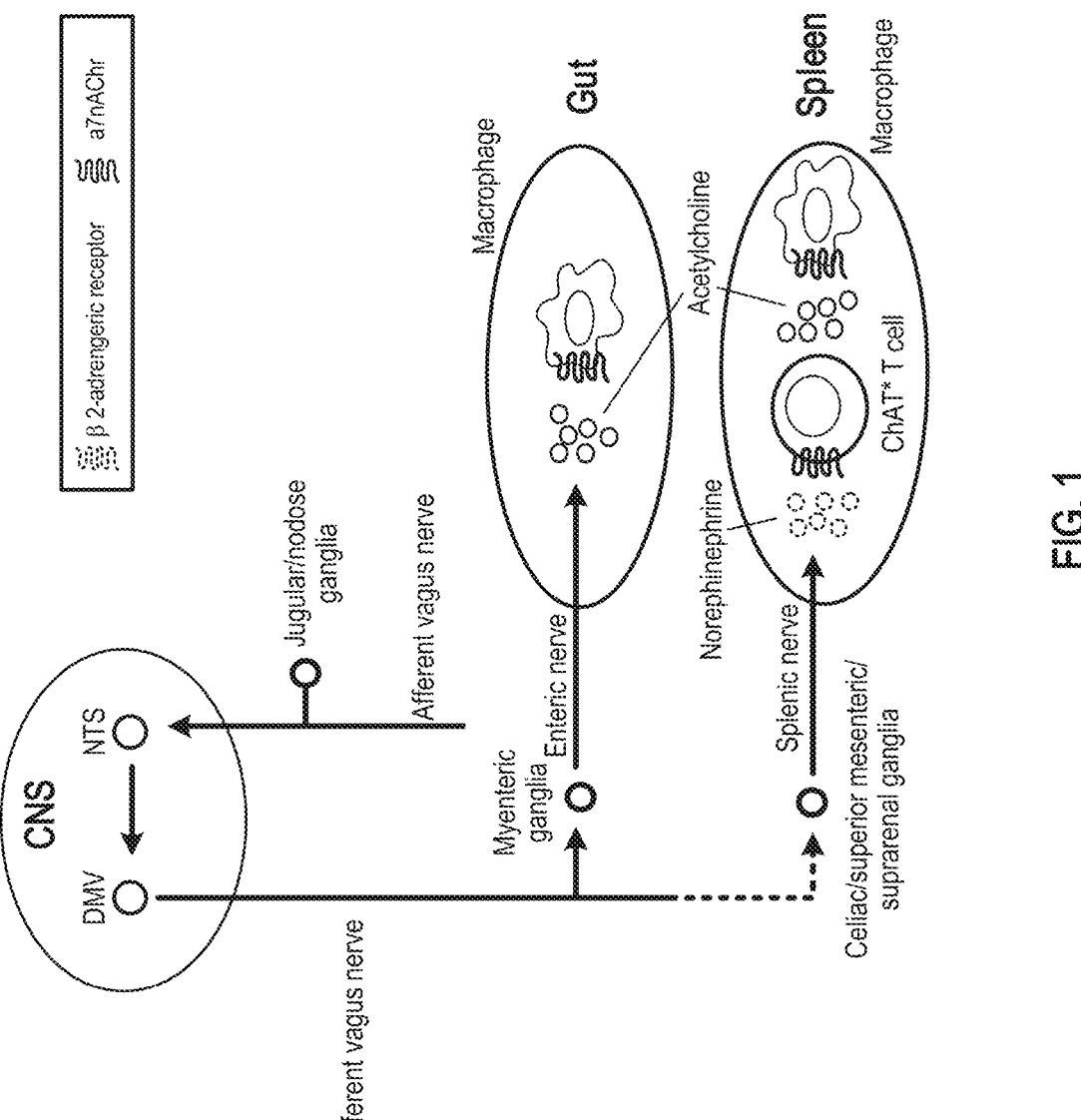
FIG. 1 shows a model of a vagus Inflammatory Reflex.

Provided herein are methods for preventing, treating, or preventing recurrence of symptoms of autism or autism spectrum disorder in a subject in need thereof, said method comprising: administering to said subject an effective amount of electrical vagus nerve stimulation (VNS). In certain embodiments, the subject exhibits inflammation or gut microbiome dysfunction. In further embodiments, the subject is refractory to standard autism treatments. In particular embodiments, the subject is a child.

Provided herein are methods for preventing, reducing or reversing chronic inflammation in children with autism, developmental abnormalities and other medical conditions comprising administering to said subject an effective amount of electrical vagus nerve stimulation (VNS). Also provided herein are methods for treating refractory symptoms or preventing recurrence of symptoms in children with autism, developmental abnormalities and other medical conditions comprising administering to said subject an effective amount of electrical vagus nerve stimulation (VNS).

The invention methods provided herein are contemplated to be safe, non-invasive, portable, and do not require certified technicians. The invention methods of preventing, reducing or reversing chronic inflammation are highly effective for improving immune modulation, restoration of neurological function, and the neurological processes involved in a child reaching the natural neurological milestones. The treatment of neurological developmental abnormalities, and any condition associated with a child's neurological and physiological developmental and growth, is within the scope of the invention methods provided herein.

As used herein, the phrase "autism or autism spectrum disorder (ASD)" refers to a neurological condition characterised by difficulty in communicating and forming relationships. Such social aspects of the disorder are frequently accompanied by physical and behavioural aspects. Due to the variety of presentations of autism, the term currently preferred is "autistic spectrum disorder" (ASD) which better reflects the range of symptoms observed within this disorder.

Defined diagnostic criteria for ASD or autistic disorder have been described for example by WHO e.g. Section F84 of ICD-10 (World Health Organisation 1992) available at http://www.who.int/classifications/icd/en/GRNBQQK.pdf, the API-R and Autism Diagnostic Observation Schedule (Generic) (ADOG) available at for example, http://www.hogrefe.co.uk^autism-diagnostic-observation-schedule-ados.html or DSM V available at http://www.dsm5.org/. The diagnostic criteria as they appear in DSM-V (May 2013) are available at https://www.autismspeaks.org/what-autism/diagnosis/dsm-5-diagnostic-criteria. For the purposes of the present invention, reliance is preferably placed in the DSM-V definitions and characterisations of ASD.

As used herein, the phrase "gut microbiome dysfunction" refers to an imbalance of the gut microbiome. The human microbiota contains 10-100 trillion symbiotic microbial cells harbored by each person, primarily bacteria in the gut, while the human microbiome consists of the genes these cells harbor. These microbial cells, and their genetic material, live with humans from birth, and every individual has a unique mix of species. This relationship is important for nutrition, immunity and effects on the brain and behavior, and has been implicated in a number of diseases where the disease is caused by a disturbance in the normal balance of microbes or where the disturbance is another downstream consequence of the disease. The interaction between the human microbiota and the environment is dynamic, meaning that microbial communities are constantly being transferred between surfaces, and that a dynamic interaction exists between environmental microbiota and different human body sites. There is increasing evidence that individuals actually share a core microbiota, with vastly different sets of microbial species yielded very similar functional molecular interactions, reactions and relation networks for metabolism, genetic information processing, environmental information processing, cellular processes, and organismal systems referred to as KEGG pathways.

Gut microbiota composition and diversity is affected by many factors, including by aging. An apparent age-related gut microbiota imbalance has been described, featuring an altered microbial diversity, a lower abundance of probiotic strains (e.g., Difidobacteria), and a reduced number of species producing butyrate, a short chain fatty acid (SCFA) that plays important metabolic functions and has a major role in maintaining the integrity of intestinal epithelium.

As used herein, the phrase "standard autism treatments" refers to current known approaches for treating autism, such as: behavioral and communication therapies, including Applied Behavioral Analysis (ABA), Speech Therapy, and Occupational Therapy; Medications, such as those for anxiety, depression, and aggression; Educational interventions: Educational interventions; and other therapies, such as dietary changes, supplements, and alternative medicines.

As used herein, the phrase "preventing, reversing or reducing inflammation" refers to the combined effect of the invention treatment methods to modulate and/or substantially reduce the levels of pro-inflammatory cytokines to within a protective range avoiding pro-inflammatory responses and, on the other hand, avoiding immunosuppression. In particular, VNS was shown to rebalance the working point of autonomic regulation of the immune system into a protective range avoiding pro-inflammatory responses and, on the other hand, avoiding immunosuppression. The "working point" is defined as the magnitude of innate immune responses relative to the infection or injury stimulus. Chronic changes can unfavorably increase or decrease the working point with the resulting overshooting immune response (with tissue damage, sepsis, or even death) or immunosuppression (with secondary infections), respectively.

When an electrical stimulus is placed on the vagus nerve within the neck or chest cavity (see, e.g., U.S. Pat. Nos. 8,918,178; and 8,843,210), the electrical impulse travels downward to all body organs via efferent nerve fibers and upward to the brain via afferent nerve fibers. The vagus nerve contains a branch called the auricular branch of the vagus nerve and is located in the subcutaneous tissue of the ear. This branch of the vagus nerve contains only afferent fibers; as such, electrical stimuli results in signals traveling only upwards into the brain.

The selective stimulation of afferent vagus nerve fibers can reduce systemic inflammation and has the added benefit of lessening the risk of side effects attributable to unregulated efferent signaling. The vagus nerve fibers are anatomically organized according to the functions they mediate and the organs they innervate. As such, non-specific stimulation of these fibers may lead to adverse effects, especially in children with autism whose nervous system is incompletely developed.

While selective stimulation of afferent auricular vagus nerve fibers, in accordance with the present invention methods, has the advantage of fewer adverse side effects, the ability to use auricular VNS stimulation over 30-60 minutes can be easily performed without the costs and increased risks of surgically implanted VNS devices commonly used for drug-resistant epilepsy.

Likewise, prior art VNS devices that discharge their electrical stimulus through the skin and muscle of the neck can be painful and would most likely trigger an avoidance response from children with autism leading to its consistent use being impractical. Because the auricular branch of the vagus nerve is within the very shallow subcutaneous tissue of the ear, VNS according to the invention methods can be performed painlessly in an autistic child who may be non-verbal and unable to voice if they are experiencing pain.

Compared to prior art implantable VNS devices, transcutaneous VNS stimulation at the auricular branch does not require the associated costs and risks associated with surgery, is generally much less expensive and uncomplicated to operate, and allows the parents to oversee treatment in the home setting.

Figure 2:
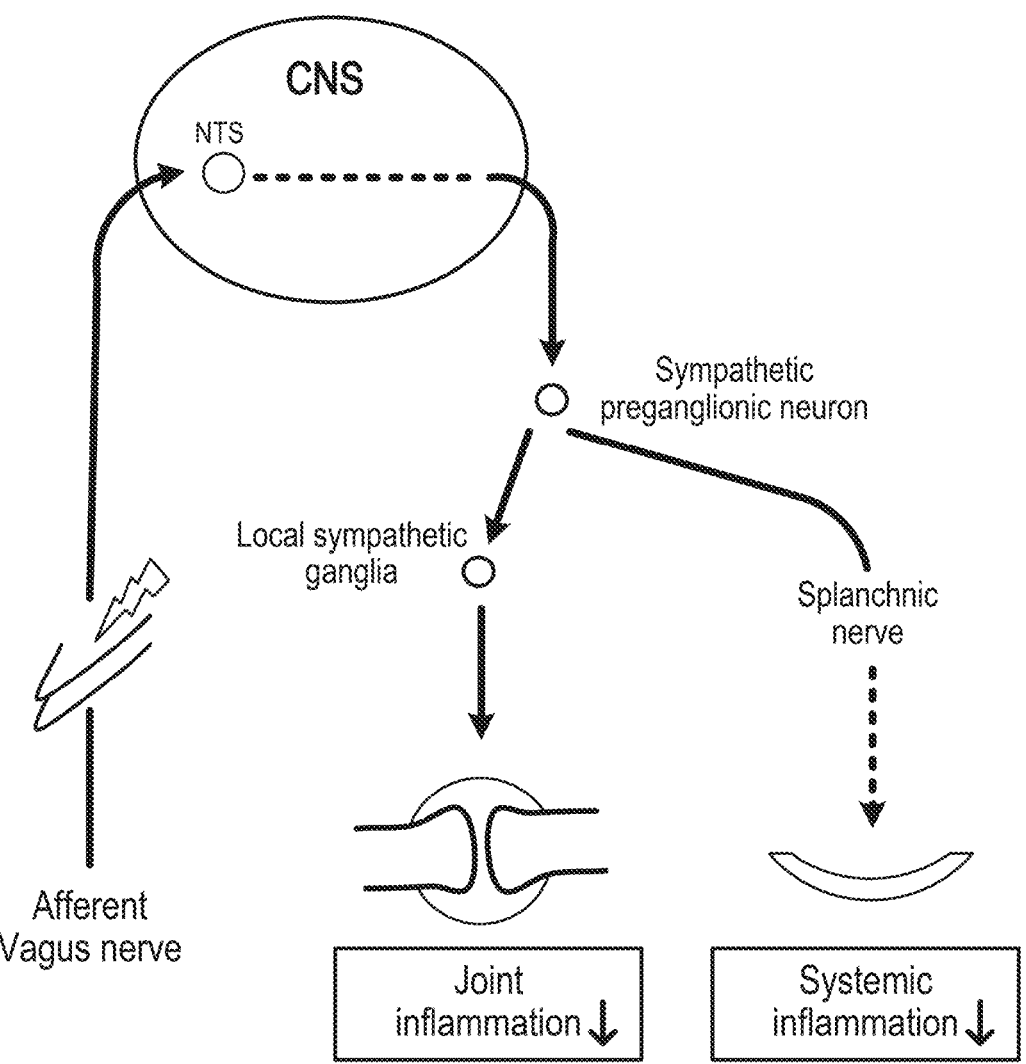
FIG. 2 shows a model of an Anti-inflammatory Sympathetic Reflex.

Stimulation of the afferent pathway of the vagus nerve can modulate inflammation through 2 separate pathways, the inflammatory reflex (FIG. 1) and the anti-inflammatory sympathetic reflex (FIG. 2). The inflammatory reflex is triggered when the afferent vagus nerve senses inflammatory products through the receptors. The nerve activity is relayed through the central nervous system (CNS) to the efferent vagus nerve. The original pathway involves the splenic nerve although a direct connection between the efferent vagus nerve and the splenic nerve is still controversial. Activated splenic nerves release norepinephrine from their terminals, which interacts with β2-adrenergic receptors expressed on the choline acetyltransferase (ChAT)-positive T cells in the spleen, causing acetylcholine (ACh) release from this specific T cell subpopulation. ACh binds to $\alpha7$ nicotinic acetylcholine receptors ($\alpha7nAChRs$) expressed on macrophages residing in close proximity to ChAT-positive T cells, resulting in suppression of proinflammatory cytokine production (e.g., TNFα) by macrophages and alleviated inflammation in many pathological settings (e.g., endotoxemia, septic shock, acute kidney injury).

Another anti-inflammatory pathway elicited by afferent vagus nerve stimulation is shown in FIG. 2. Afferent vagus nerve stimulation can elicit an anti-inflammatory pathway involving sympathetic efferent pathways through the central nervous system (CNS). In a model of joint inflammation, the local release of norepinephrine from sympathetic nerve terminals within joints alleviates inflammation. On the other hand, the splanchnic sympathetic nerve seems to be important to suppress systemic inflammation after lipopolysaccharide (LPS) administration. Direct target(s) of the splanchnic nerve is not clear.

In certain embodiments, the present invention methods relate to the reversal of acute and chronic autonomic dysfunction by the suppression of pro-inflammatory cytokines, namely interleukin-1 (IL-1), interleukine-6 (IL-6) and tumor necrosis factor-alpha (TNF-alpha). The pro-inflammatory cytokines are reduced through the cumulative effect of reversing intestinal bacterial overgrowth, normalizing dietary intake of omega-6 and omega-3 fatty acids, supplementation with oleic acid, intermittent restriction of caloric intake, and stimulation of the acetylcholine inflammatory reflex by transcutaneous vagal nerve stimulation (tVNS). If this proves initially inadequate, additional steps to reduce pro-inflammatory cytokines include supplementation with curcumin and/or the introduction of carbohydrate restriction and/or intermittent fasting.

As used herein, the phrase "excess inflammation" refers to an overproduced and unregulated immune response that releases excess amounts of cytokines in the body. Under a normal immune response, non-excess amounts of cytokines are released by cells of the immune system to help fight infection. In the case of excess inflammation, the reaction becomes uncontrolled, and it is believed that too many immune cells are activated in a single location causing excessive inflammation.

Excess inflammation can be caused by a wide variety of infectious and noninfectious diseases; and also result from attempts at therapeutic intervention. Excess inflammation may also underlie certain neurological diseases, including neurodegenerative diseases. In children, excess inflammation is thought to underlie autism, autism spectrum disorders, and other neurological developmental disorders. In some cases, the excess inflammation involved in autism and autism spectrum disorders is thought to be associated with disruption of the gut-brain axis, for example through disruption or dysregulation of the gut microbiome. Autonomous nerve activity is also thought to play a role in this regulation and homeostasis of the gut-brain axis.

As used herein, the phrase "vagus nerve stimulation" or "VNS" refers to the stimulation of the auricular branch of the vagus nerve. The vagus nerve can be stimulated using methods well known in the art, including internally via a transplanted device (e.g., U.S. Pat. No. 9,211,410; incorporate herein by reference in its entirety), mechanically, or transcutaneously. Transcutaneous vagus nerve stimulation (tVNS) of the auricular branch of the vagus nerve results in the reduction of pro-inflammatory cytokines via the cholinergic anti-inflammatory pathway (Lerman et al., Neuromodulation 19:283-291, 2016; incorporated herein by reference in its entirety). As used herein, the term "vagus nerve" is used in its broadest sense, and includes any nerves that branch off from the main vagus nerve, as well as ganglions or postganglionic neurons that are connected to the vagus nerve. The vagus nerve is also known in the art to carry the parasympathetic nervous system impulses through its branches. The advantages of vagus nerve stimulation over the use of pharmaceutical agents are set forth in Table 1.

TABLE 1

| Pharmaceutical Agents | vagus Nerve Stimulation (VNS) |
| --- | --- |
| Few options | Effective |
| Expensive | Human and animal data |
| Increased risk of | Regulates cytokine release |
| infection with | Safe |
| immunosuppressive | No increased risk of infections |
| agents | Improves inflammation regulation |
| | Does not "suppress" immune system |
| | Transcutaneous Stimulation (tVNS) |
| | Simple; minimal training |
| | Inexpensive; easily manufactured |
| | Reusable |

In certain other embodiments, the vagus nerve can be stimulated by any means known to those of skill in the art. Nonlimiting examples include: mechanical means such as a needle, ultrasound, or vibration, magnetic field exposure, and heat/cold exposure. Mechanical stimulation can also be carried out by carotid massage, oculocardiac reflex, dive reflex and valsalva maneuver. The efferent vagal nerve fibers can also be stimulated by electromagnetic radiation such as infrared, visible or ultraviolet light; heat, or any other energy source. The efferent vagus nerve can be stimulated by stimulating the entire vagus nerve (i.e., both the afferent and efferent nerves), or by isolating efferent nerves and stimulating them directly. The latter method can be accomplished by separating the afferent from the efferent fibers in an area of the nerve where both types of fibers are present. Alternatively, the efferent fiber is stimulated where no afferent fibers are present, for example close to the target organ served by the efferent fibers.

The efferent vagus nerve fibers can also be stimulated by stimulating the target organ directly, e.g., electrically, thus stimulating the efferent fibers that serve that organ. In other embodiments, the ganglion or postganglionic neurons of the vagus nerve can be stimulated. In preferred embodiments set forth herein, the vagus nerve is stimulated electrically, using any electrical means known to those of skill in the art. For example, commercial vagus nerve stimulators for use herein include electro-acupuncture, the Cyberonics NCP®, the NEMOS® device for t-VNS, or a transcutaneous electrical nerve stimulation (TENS) unit, such as the TENS 7000 (Roscoe Medical, Strongsville, OH), and the like.

In combination with the methods provided herein, the amount of stimulation useful to inhibit inflammation, and thus treat or prevent the conditions described above, including symptoms associated with autism and autism spectrum disorders, can be determined by the skilled artisan utilizing the description herein, without undue experimentation. In one embodiment, to prevent, treat, or prevent recurrence of symptoms associated with autism or autism spectrum disorders, a constant voltage stimulation of about 1 to 5 V, at 2 ms and 1 Hz, for 10 minutes is contemplated herein to inhibit the inflammation sufficiently and thereby prevent, treat, or prevent recurrence of symptoms.

In certain embodiments, the electrical stimulation is achieved by clipping electrodes across the tragus of the ear, inducing an electrical current with a TENS (transcutaneous electrical nerve stimulation) unit with the frequency in the range selected from about 0.1 Hz to about 30 Hz, about 0.3 Hz to about 25 Hz, about 0.5 Hz to about 20 Hz, about 0.7 Hz to about 15 Hz, about 0.9 Hz to about 10 Hz, about 1.0 Hz to about 9 Hz, about 1.2 Hz to about 8 Hz, about 1.4 Hz to about 7 Hz, about 1.6 Hz to about 6 Hz, or about 2 Hz to about 5 Hz. In other embodiments, the frequency is in the range selected from about 1 Hz to about 30 Hz, about 2 to about 25 Hz, about 3 to about 20 Hz, about 4 to about 15 Hz, and about 5 to about 10 Hz pulse frequency; with about 5 to about 10 Hz pulse frequency being most commonly used.

In these embodiments the pulse width can be in the range selected from about 20 to about 1000 μs, about 30 to about 900 μs, about 40 to about 800 μs, about 50 to about 700 μs, about 60 to about 600 μs, about 70 to about 500 μs, about 80 to about 450 μs, about 90 to about 400 μs, about 100 to about 350 μs, about 110 to about 325 μs, about 120 to about 300 μs, about 130 to about 275 μs, about 140 to about 260 μs, or about 150 to about 250 μs. In other embodiments, the pulse width can be in the range selected from about 100-800 μS, 125-750 μS, 150-700 μS, 175-650 μS, 200-600 μS, 225-550 μS and 250-500 μS pulse duration; with 250-500 μS pulse duration most commonly used.

In these embodiments, the current can be in a range selected from about 0.1 to about 5.0, about 0.2 to about 4.0, about 0.3 to about 3.0, about 0.4 to about 2.0, or about 0.5 to about 1.0 mAmps. In a particular embodiment, the electrical stimulation is achieved by inducing an electrical current with a TENS (transcutaneous electrical nerve stimulation) unit with the frequency at 5-10 Hz, pulse width at 100-800 μs and 0.5-1.0 mAmps. In another embodiment, a range of about 0.1 to about 4.8 mA output current is employed; and the currents are dosed between currents slightly below the perceptive threshold all the way up to the maximally tolerated current by the subject (with at or just below the perceptive threshold are most common).

It is contemplated herein, that the tVNS is employed for an amount of time sufficient to adequately reduce the pro-inflammatory cytokines via the cholinergic anti-inflammatory pathway. Suitable dosing regimens can range from a single 5-minute stimulation once daily to repeated 5-minute stimulations every 4-6 hours. In further embodiments, the stimulation or treatment can range from about 2 to 10 minutes, from about 3 to 8 minutes, from about 4 to 7 minutes, or about 5-6 minutes. In other embodiments, the individual stimulation doses can range from: about 30 sec to about 5 min; from about 45 sec to about 4.5 mins; about 1 min to about 4 min; about 1.5 to about 3.5 min; about 2 min to about 3 min. In other embodiments, the individual stimulation doses can range from: about 30 sec to about 5 min; from about 30 sec to about 4.5 mins; about 30 sec to about 4 min; about 30 sec to about 3.5 min; about 30 sec to about 3 min; about 30 sec to about 2.5 min; about 30 sec to about 2 min; about 30 sec. to about 1.5 min; about 30 sec to about 1 min; and the like. In yet further embodiments, the stimulations or treatments can be administered multiple times daily, such as once: every hour, every 2 hours, every 3 hours, every 4 hours, every 5 hours, every 6 hours, every 8 hours, every 10 hours, every 12 hours, or every 24 hours (e.g., once daily, and the like). In another embodiment, the number of stimulations or treatments per day can be selected from the group consisting of 1, 2, 3, 4, 5, 6, 7, 8, 9, 10, 11, 12, 13, 14, 15, 16, 17, 18, 19, 20 treatments per day.

The length of treatment can be as long as is necessary to achieve the effect of preventing, treating, or preventing recurrence of symptoms of autism or autism spectrum disorder in a subject or patient; such as for example, 1 to 120 months, 1 to 96 months, 1 to 72 months, 1 to 48 months, 1 to 24 months, 1 to 12 months. In a particular embodiment, the treatment is performed until the symptoms of subject receiving the treatment resolve; such treatment can be for months or years, up to and including the lifetime of the subject. In a particular embodiment, the treatment is performed to prevent or to prevent the recurrence of symptoms for any number of days, months, or years, up to and including the lifetime of the patient. In another embodiment, the subject receives 1-2, 5-minute treatments per day for 48 months. In embodiments, such symptoms include deficits in attention, awareness, eye contact, constipation, potty training, reading competency, mathematical competency, learning, intellect, comprehension, memory recall, emotional regulation, anxiety, aggression, self-injurious behavior, violent behavior, impulse control, hyperactivity, dietary preferences, and/or socialization.

In other embodiments, severe inflammatory states are contemplated herein to benefit from a continuous on-off cycling regimen with repetitive continuous electrical impulses (e.g., for 2 to 10 minutes, 5 minutes, or the like) followed by a 30-second to 5-minute off-phase (no current). For example, an on-off-on-off continuum for 24 hours per day, and the like. As other examples, this particular embodiment contemplates administering an electrical impulse once every 5.5. mins., 6.5 mins., 7 mins., 7.5 mins., 8 mins., 8.5 mins., 9 mins., 9.5 mins., 10 mins., 15 mins., 20 mins., 25 mins., 30 mins., 35 mins., 40 mins., 45 mins., 50 mins., 55 mins., and 60 mins. (e.g., every hour, and the like).

In a particular embodiment, the various elements of the electrical current used for inflammation modulation are:

1-30 Hz pulse frequency (5-10 Hz most commonly)

100-800 μs pulse duration (250-500 μs μs most commonly)

0.1-4.8 mA output current. Currents are dosed between currents slightly below the perceptive threshold of the subject all the way up to the maximally-tolerated current by the subject (at or just below the perceptive threshold are most common)

30-sec-5 min. individual stimulation doses 10-100 V voltage output

Biphasic Waveform taVNS Device and System

Figure 9:
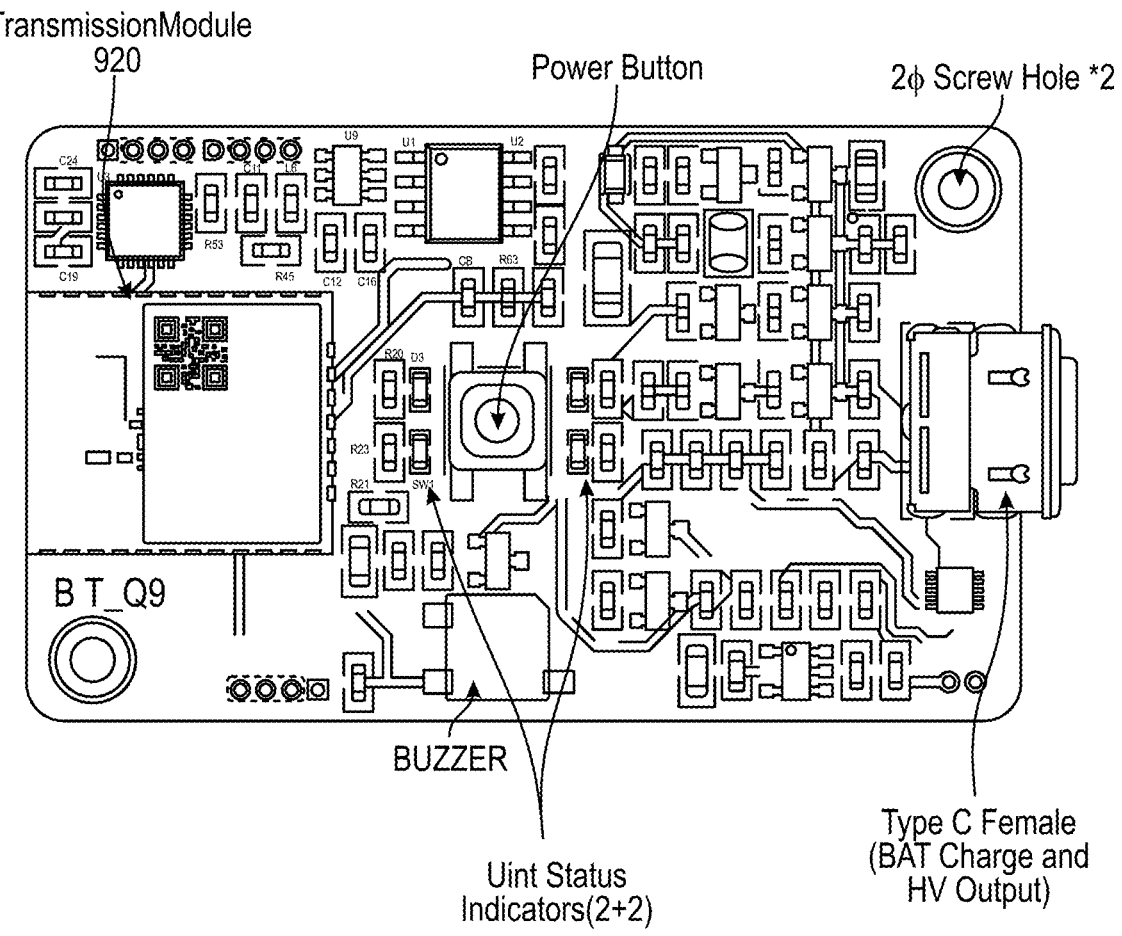
FIG. 9 shows components of a power source for a taVNS system in accordance with some aspects of the disclosure.
Figure 10:
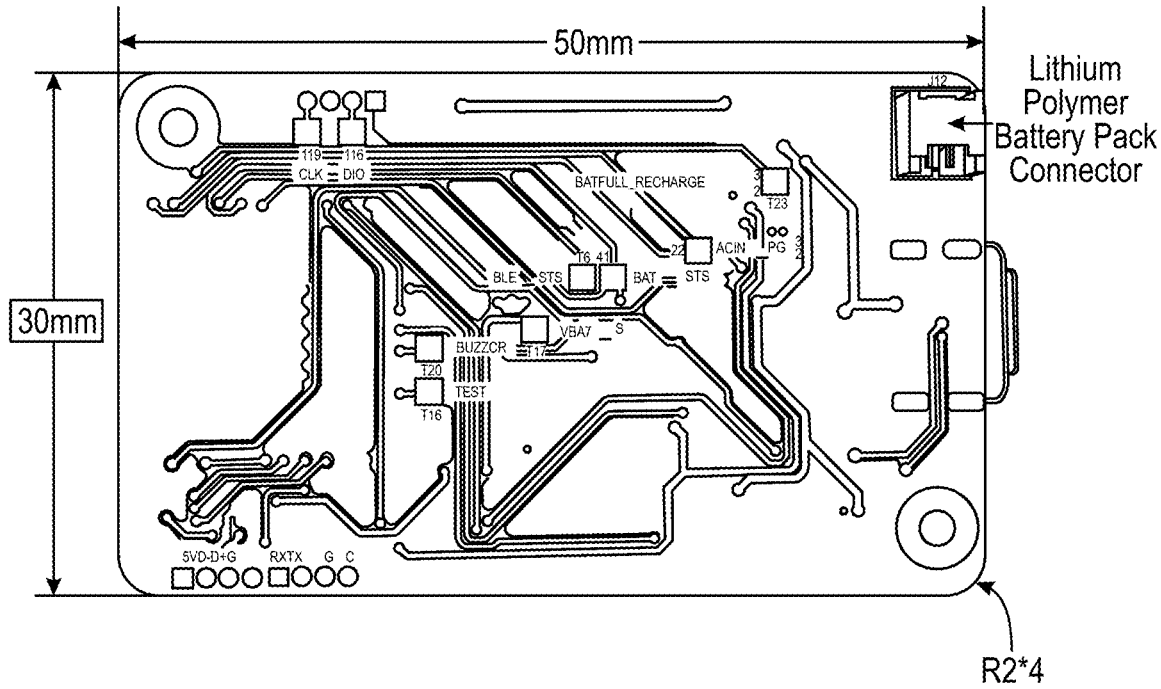
FIG. 10 shows a second view of the components of the power source for a taVNS system in accordance with some aspects of the disclosure.

Provided herein is a taVNS system comprising an earclip that, when attached to an ear, provides two electrical contacts on opposite sides of the ear (e.g., on opposite sides of the tragus or the concha). FIG. 9 shows components (e.g., a circuit board and associated processors(s), interfaces, ports, and other functional components) of a power source (e.g., a source of adjustable electrical pulses) for a taVNS system in accordance with some aspects of the disclosure. FIG. 10 shows a second view of the components of the power source for a taVNS system in accordance with some aspects of the disclosure. FIG. 11 shows additional views of a housing for the power source 1110 of the taVNS system and how the components shown in FIGS. 9 and 10 may be arranged in the housing in accordance with some aspects of the disclosure. The taVNS system, in some aspects, further comprises a power source 1110 (also referred to as a powersource) that may be electrically connected to the earclip and includes at least one processor 910 configured to provide adjustable electrical pulses via the two electrical contacts, and a wireless communication device 920 configured to communicate with a wireless device (e.g., a parent's mobile device) and the at least one processor 910 (where the communication with the at least one processor 910 may be via wired connections, e.g., via the circuit board). In some aspects, the wireless communication device 920 may be configured to receive, from the wireless device, configuration information (e.g., stimulation parameters) for configuring the adjustable (or configurable) electrical pulses and to provide the configuration information to the at least one processor 910. The taVNS system, in some aspects, may further comprise (or be associated, or used in conjunction, with) the wireless device (e.g., a mobile device, cell phone, tablet, etc.), where the wireless device may be configured to execute an application used to specify the configuration information and may further be configured to provide the configuration information to the wireless communication device of the power source. The wireless device, in some aspects, may provide the configuration information via Bluetooth or via a Wi-Fi connection (e.g., via the internet or other intermediate system connected to both the wireless device and the wireless communication device). The taVNS system, in some aspects, may comprise a power source (e.g., power source 1110) that is controlled via Bluetooth connectivity with a wireless device (e.g., a parent's mobile phone or electronic tablet). In a particular embodiment, the power source may include a rechargeable battery. In a particular embodiment, an advantage of the invention taVNS system is that a child cannot activate the device or alter stimulation settings since these are all controlled by the parent's device having the operating system or an application controlling the power source.

In some aspects, the power source may be electrically connected to the earclip via an electrical wire (e.g., a short cord that is less than one of 24, 23, 22, 21 20, 19, 18, 17, 16, 15, 14, 13, 12, 11, 10, 9, 8, 7, 6, 5, 4, 3, or 2 inches) from the power source to the earclip. The electrical wire, in some aspects, is short enough to eliminate the risk of strangulation should the parent leave a child unattended while using the device. In other embodiments, electrical wire cord is less than one of 12, 11, 10, 9, 8, 7, 6, 5, 4, 3, or 2 inches. In other embodiments, electrical wire cord is less than one of 10, 9, 8, 7, 6, 5, 4, 3, or 2 inches. In other embodiments, electrical wire cord is less than one of 8, 7, 6, 5, 4, 3, or 2 inches. In other embodiments, electrical wire cord is less than one of 6, 5, 4, 3, or 2 inches.

Compared to prior art devices that are handheld against the neck while only delivering one to a few impulses, the invention taVNS system delivers continuous electrical stimulation (e.g., delivers electrical pulses (continuously) for a configured duration at a configured frequency). In some aspects, the configurable electrical pulses are configured to provide afferent, but not efferent, electrical stimulation. Another advantage of the invention taVNS system, is the avoidance pain from the electrical pulses provided.

In particular embodiments, the power source of the taVNS system can be controlled by applications operating on standard operating systems, e.g., either iOS or Android, or the like. The application or an operating system of the taVNS system may be resident within or executing on, a phone, tablet, or another specialized device (e.g., iPod and the like). In particular embodiments, the rechargeable batteries used in the power source are selected to provide long-term battery life, such that recharging is required 1-2 times per month for average use.

In particular embodiments, each taVNS system has a unique identifying serial number and can be monitored remotely via an operating system that controls the taVNS system, such as a smartphone app, and the like. For example, in some aspects, the power source may include a monitoring component that may be configured to determine whether the earclip is connected to a user while providing the configurable electrical pulses and to transmit (e.g., via a wireless communication device 910) monitoring information regarding whether the earclip is connected to the user to the wireless device (e.g., the parents mobile device) and the configuration of the configurable electrical pulses. The wireless device (e.g., the parent's mobile device or the application running on the device), in some aspects, may be configured to provide, based on the monitoring information, additional monitoring information to a remote monitoring system. In some aspects, the additional monitoring information may include first configuration information associated with a set of configurable electrical pulses provided by the taVNS system or the power source and whether the earclip was connected to the user while providing the set of configurable electrical pulses. This remote control functionality provides numerous advantages to clinicians and researchers needing to monitor the frequency and timing of taVNS system use. For example, by remotely measuring (or monitoring) the frequency of activation, time of day, the length of activation, and alterations to the current resistance, of the taVNS system, researchers and clinicians can determine if the device is effectively in contact with the skin (i.e., being used when activated).

Figure 12:
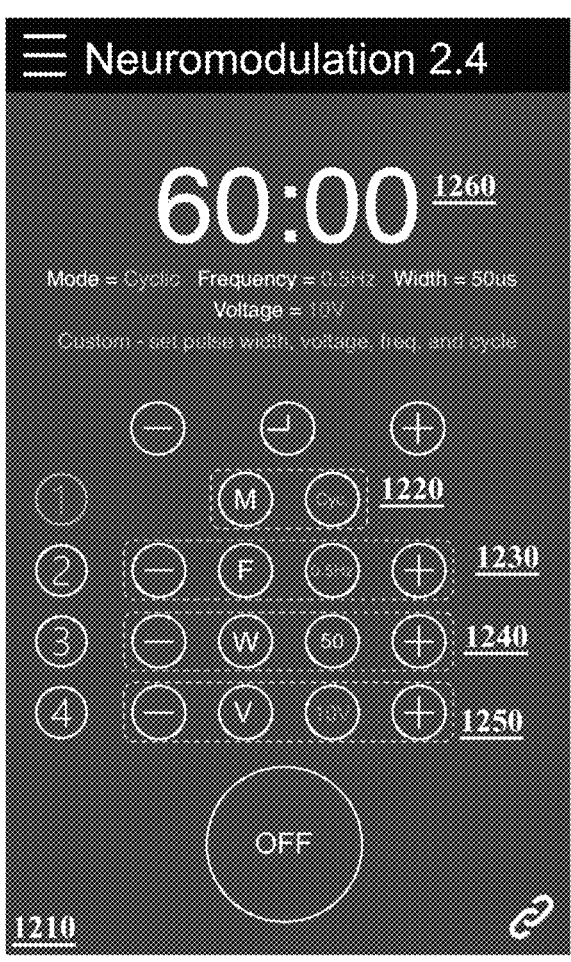
FIG. 12 shows an example of a user interface that may be provided to configure the stimulation parameters in accordance with some aspects of the disclosure.

FIG. 12 shows an example of a user interface that may be provided to configure the configurable electrical pulses in accordance with some aspects of the disclosure. For example, an application running on a smartphone may provide a user interface 1210 to adjust a duration 1260 associated with providing the configurable electrical pulses, a voltage 1250 associated with each of the configurable electrical pulses, a frequency 1230 of the configurable electrical pulses, a mode of operation 1220, and a pulse width 1240 of each of the configurable electrical pulses (collectively referred to, in some aspects, as stimulation parameters). The user interface 1210, in some aspects may further provide controls for monitoring criteria, where the stimulation parameters and monitoring criteria, in some aspects, may depend on the clinical circumstances and future medical advances in electroneuromodulation.

Other advantages of the invention taVNS system having remote monitoring and/or control capability, may include (1)

that remote monitoring allows the device to be activated or de-activated when used in a subscription model and (2) that remote control allows the device to be updated (e.g., receive a software update) as improvements are made to the software. Accordingly, in some aspects the wireless device, or the wireless communication device of the power source, may be further configured to receive activation information from the remote monitoring system, where the activation information comprises one of a first indication for the system to provide a first additional set of configurable electrical pulses or a second indication to stop providing a second additional set of configurable electrical pulses.

Earclip Specifications

Figure 13:
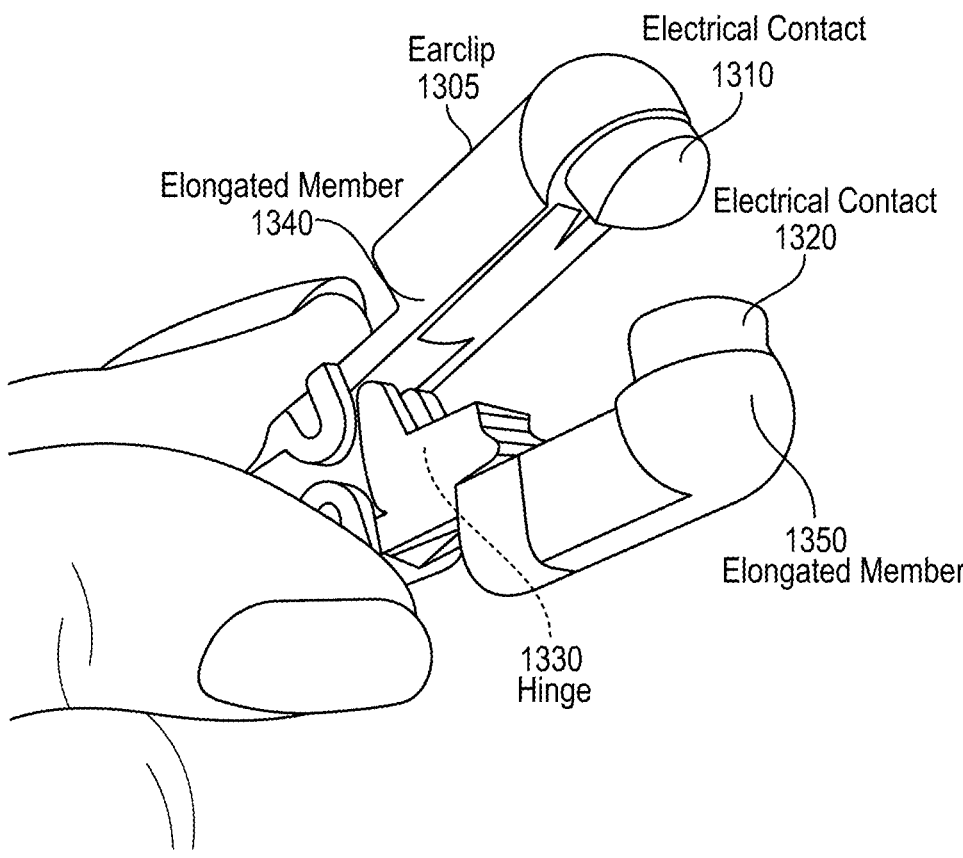
FIG. 13 shows an example earclip in accordance with some aspects of the disclosure.

FIG. 13 shows an example earclip 1305 in accordance with some aspects of the disclosure. In some aspects, the earclip may be in the form of a clip used to secure the earclip 1305 to an ear of a user. The earclip may include a first electrical contact 1310 and a second electrical contact 1320 comprising a pair of electrical contacts (e.g., electrodes) used to transmit an electrical current and stimulate the auricular branch of the vagus nerve through the skin of the ear; which is also referred to as transcutaneous vagus nerve stimulation (tVNS).

The vagus nerve carries signals for the parasympathetic branch of the autonomic nervous system. Electrical stimulation of the vagus nerve activates the parasympathetic nervous system, and results in the reduction of inflammation within the central nervous system as well as throughout the entire body. Vagus stimulation also induces the brain to restore lost neuronal pathways through a process called neuroplasticity.

In the U.S., there are presently over 100,000 individuals who have had vagus nerve stimulators implanted within their chests (the leads wrap around the vagus nerve as it descends through the chest) for treatment-resistant depression and epilepsy. Implanted VNS has received FDA approval for use in treatment-resistant depression and epilepsy, and more recently for obesity.

Stimulation of the auricular branch of the vagus nerve has equivalent effects on the parasympathetic nervous system when compared to the implantable unit but obviously does not require an invasive surgical procedure and is very inexpensive ($185 for a transcutaneous VNS vs approx. $45,000 for an implantable device.).

In some embodiments, the invention earclip and/or system for transcutaneous auricular vagal nerve stimulation (taVNS) is contemplated to induce recovery of the autonomic nervous system when used as part of the Nemechek Protocol for Autonomic Recovery (see U.S. Pat. No. 10,335, 396; which is incorporated herein by reference for all purposes). In other embodiments, the invention earclip and/ or system for transcutaneous auricular vagal nerve stimulation (taVNS) is contemplated to induce neuroplasticity in athletes to improve athletic performance. For example, an athlete may wear the clip while undergoing VNS during the specific skill they want to improve.

Overall clip design should approximate the function of the earclip illustrated in FIG. 13. For example, in some aspects, the earclip 1305 (or earpiece) may generally have a c-shape, a central axis point acting as a hinge (e.g., hinge 1330), and a spring-like action similar to the manner in which a common clothes-pin functions. While one example is presented in FIG. 13, in some aspects, possible modifications to basic design include: (1) a more streamlined modern appearance, (2) having the wires extend downward closer to the body or upward up and over the ear, (3) having a wired dongle protruding from the clip into which the TENS cables could plug into, (4) having the soft electrical contacts (1310 and 1320) be of varying shapes and sizes so the user could use the combination that provides best grip, contact and comfort, and/or (5) the clip being able to be used for placement in either the tragus or concha (as discussed below in relation to FIGS. 15A and 15B).

In particular embodiments, the electrical contacts suitable for use in the invention earclips are made of silicone rubber compounds, such as KE-3601SB-U; KE-3711-U, KD-3801M-U, and the like (commercially available from Shin-Etsu Chemical Co., Ltd., Tokyo, JP). The general physical properties of exemplary suitable silicone rubber compounds for use in making the soft electrical contacts of the invention earclip are set forth in FIG. 18.

Figure 14:
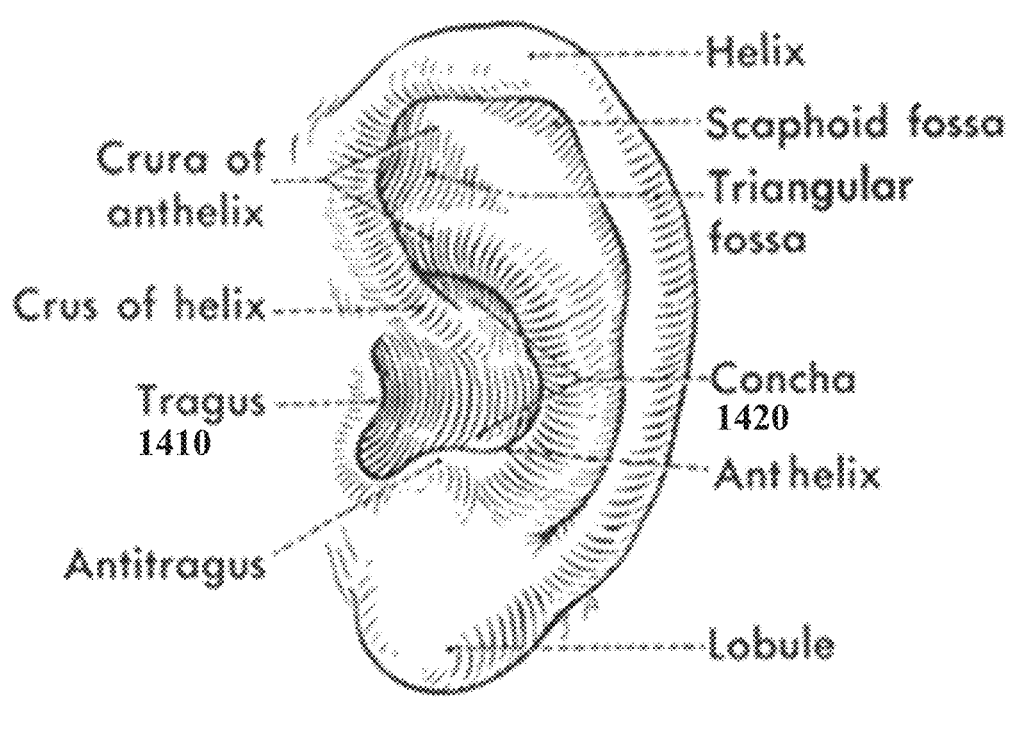
FIG. 14 shows aspects of the ear relevant to the placement of the earclip in some aspects of the disclosure.
Figure 15A:
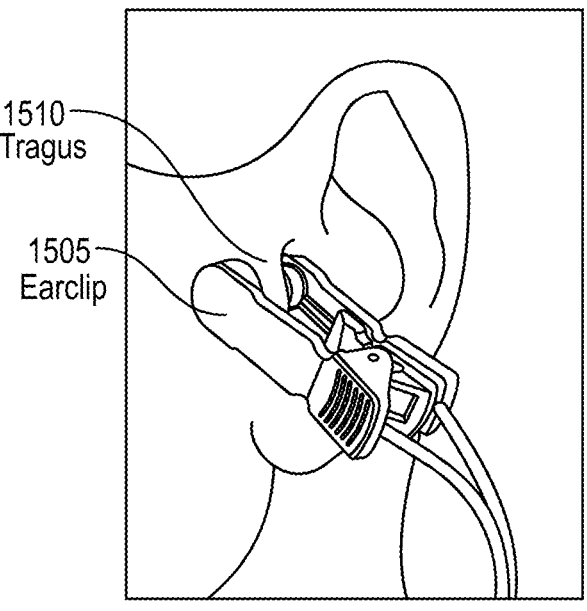
FIG. 15A shows a first configuration for attaching an earclip to a tragus of an ear.
Figure 15B:
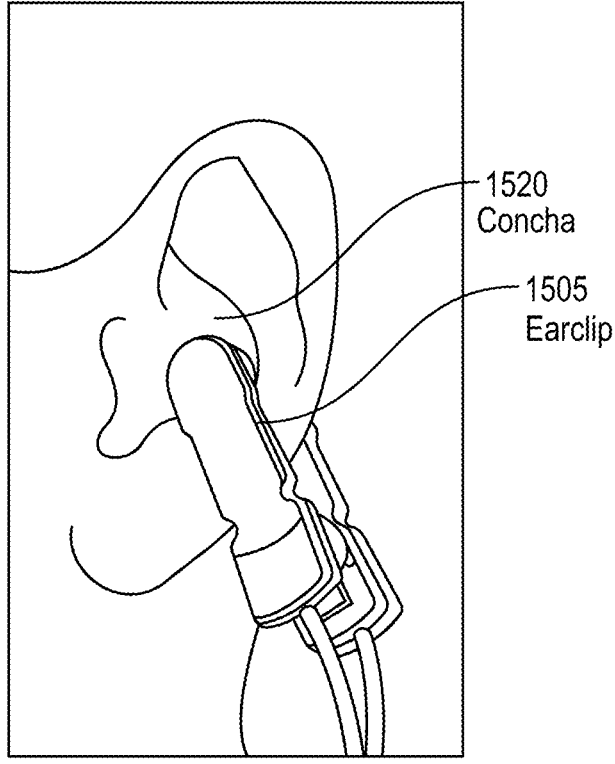
FIG. 15B shows a second configuration for attaching an earclip to a concha of an ear.

FIG. 14 illustrates aspects of the ear relevant to the placement of the earclip in some aspects of the disclosure. For example, FIG. 14 illustrates a tragus 1410 and a concha 1420 that may be targets for placement of the electrical contacts of the earclip (e.g., electrical contact 1310 and 1320 of earclip 1305 of FIG. 13). FIG. 15A illustrates a first configuration for attaching an earclip 1505 to a tragus 1510 of an ear. FIG. 15B illustrates a second configuration for attaching an earclip 1505 to a concha 1520 of an ear. As shown in FIG. 15A, in some aspects, the earclip 1505 may be able to clamp across the tragus with the electrical conduction pads making contact to opposite aspects of the tragus of a single ear. Additionally, as shown in FIG. 15B, the same earclip 1505 may also be able to clamp on either side of the concha (e.g., with a first electrical pad or contact (e.g., electrical contact 1310) within the concha of the ear with the opposite pad (e.g., electrical contact 1320) making electrical contact to the posterior aspect of the same ear.

In some aspects, the clip may be able to be attached to the ear without undue effort on the part of the user and the contact points should be able to efficiently transmit electrical impulses to the skin. In some aspects, the earclip may be configured to transmit the electrical impulse generated by a device (e.g., the adjustable electrical pulses generated by the power source described above in relation to FIGS. 9-12) with a current of 0.5-8.0 mA, at a frequency of 2-20 Hz, with a pulse width of 150-500 µs, and for a total daily use of 2-6 hours.

In some aspects, the earclip (or taVNS system) may be designed and/or configured to be worn comfortably for at least 120 minutes, e.g., to be worn for at least 120 minutes without causing the user to experience pain caused by excessive pressure of the earclip or any other aspect of the taVNS system design.

Figure 16A:
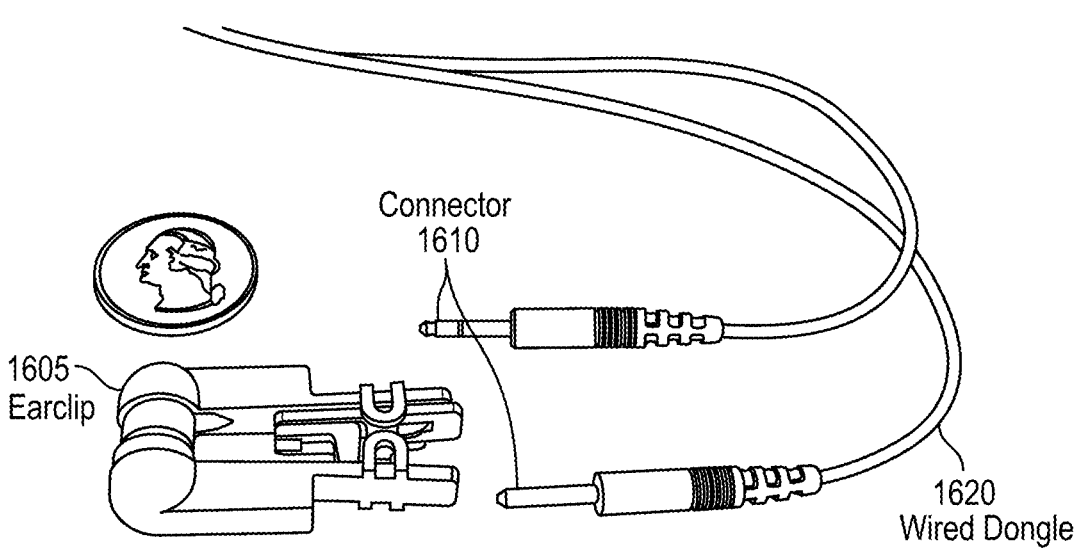
FIG. 16A shows an earclip and connectors that may be compatible in accordance with some aspects of the disclosure.
Figure 16B:
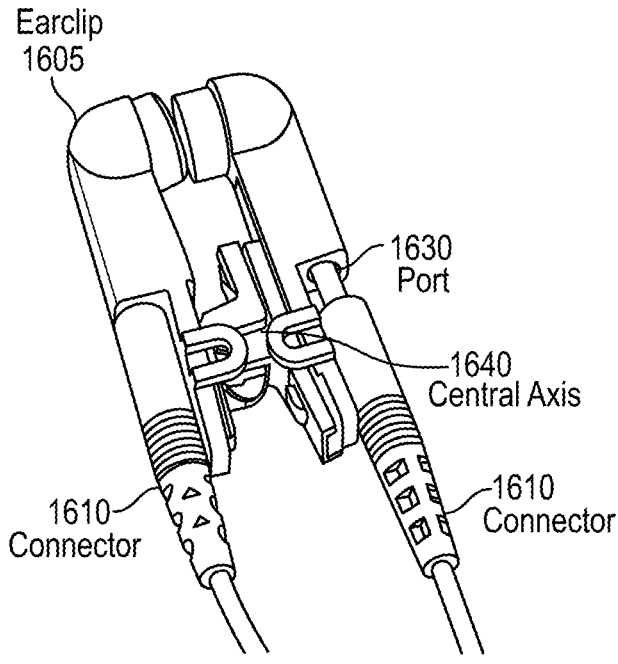
FIG. 16B shows the earclip when connected to the connectors.

The earclip, in some aspects, may be configured to be compatible with the metal rod end of cables that are commonly used with TENS units. FIG. 16A illustrates an earclip 1605 and connectors 1610 that may be compatible in accordance with some aspects of the disclosure. FIG. 16B illustrates the earclip 1605 when connected to the connectors 1610.

Provided herein is an earclip for taVNS, comprising a first electrical contact on a first elongated member 1340 and a second electrical contact on a second elongated member 1350 forming a pair of electrical contacts opposite each other; a central axis 1640 of the first and second elongated member forming a hinge 1330 under torsional-pressure, with pressure sufficient to maintain contact between each of the first and second electrical contacts and an ear lobe; a port 1630 within each elongated member to receive electricity. In particular embodiments, the electrical contacts are electrodes. In one embodiment, the torsional-pressure is applied via a spring. In particular embodiments, the electrodes are made of an electrically conductive silicone rubber compound. In particular embodiments, the electricity is received via TENS cables or a wired dongle 1620.

Hardware

Figure 17:
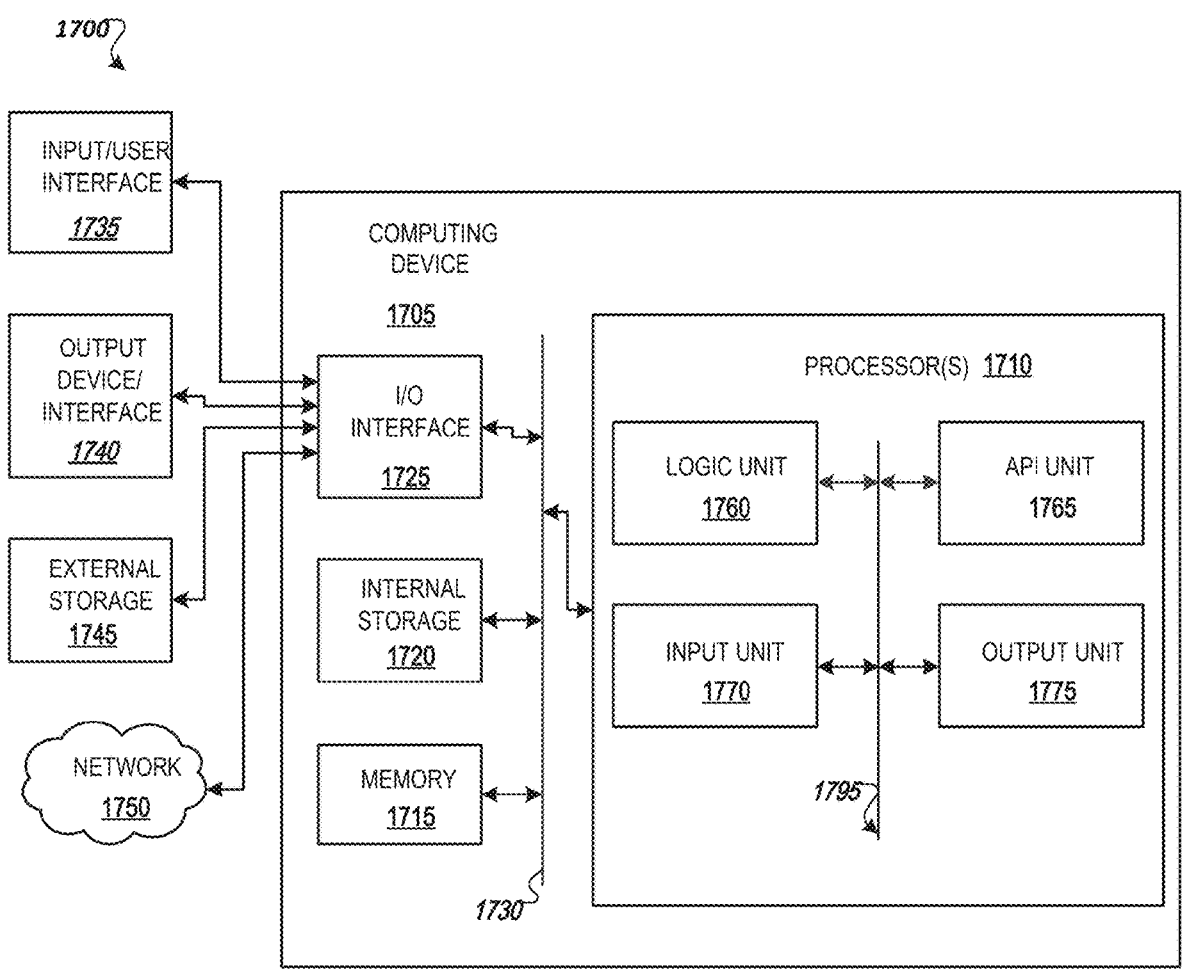
FIG. 17 shows an example computing environment with an example computer device suitable for use in some example implementations.

FIG. 17 illustrates an example computing environment with an example computer device suitable for use in some example implementations. Computer device 1705 (e.g., a computer device of the powersource 1110) in computing environment 1700 can include one or more processing units, cores, or processors 1710, memory 1715 (e.g., RAM, ROM, and/or the like), internal storage 1720 (e.g., magnetic, optical, solid-state storage, and/or organic), and/or IO interface 1725, any of which can be coupled on a communication mechanism or bus 1730 for communicating information or embedded in the computer device 1705. IO interface 1725, in some aspects, may also be configured to receive configuration information from, or transmit reporting/monitoring information to, one or more external devices (e.g., via integrated wireless communication devices for communicating with external wireless devices).

Computer device 1705 can be communicatively coupled to input/user interface 1735 and output device/interface 1740 (e.g., that may be part of, or include, a wireless communication device similar to wireless communication device 920). Either one or both of the input/user interface 1735 and output device/interface 1740 can be a wired or wireless interface and can be detachable. Input/user interface 1735 may include any device, component, sensor, or interface, physical or virtual, that can be used to provide input (e.g., buttons, touch-screen interface, keyboard, a pointing/cursor control, microphone, camera, braille, motion sensor, accelerometer, optical reader, and/or the like). Output device/interface 1740 may include a display, television, monitor, printer, speaker, braille, buzzer, adjustable electrical pulse output, or the like. In some example implementations, input/user interface 1735 and output device/interface 1740 can be embedded with or physically coupled to the computer device 1705. In other example implementations, other computer devices may function as or provide the functions of input/user interface 1735 and output device/interface 1740 for a computer device 1705.

Examples of computer device 1705 may include, but are not limited to, highly mobile devices (e.g., smartphones, devices in vehicles and other machines, devices carried by humans and animals, the powersource of the taVNS system, and the like), mobile devices (e.g., tablets, notebooks, laptops, personal computers, portable televisions, radios, and the like), and devices not designed for mobility (e.g., desktop computers, other computers, information kiosks, televisions with one or more processors embedded therein and/or coupled thereto, radios, and the like).

Computer device 1705 can be communicatively coupled (e.g., via IO interface 1725) to external storage 1745 and network 1750 for communicating with any number of networked components, devices, and systems, including one or more computer devices of the same or different configuration. Computer device 1705 or any connected computer device can be functioning as, providing services of, or referred to as a server, client, thin server, general machine, special-purpose machine, or another label.

IO interface 1725 can include but is not limited to, wired and/or wireless interfaces using any communication or IO protocols or standards (e.g., Bluetooth, Ethernet, 1702.11x, Universal System Bus, Wi-Fi, WiMax, modem, a cellular network protocol, and the like) for communicating information to and/or from at least all the connected components, devices, and network in computing environment 1700. Network 1750 can be any network or combination of networks (e.g., the Internet, local area network, wide area network, a telephonic network, a cellular network, satellite network, and the like).

Computer device 1705 can use and/or communicate using computer-usable or computer readable media, including transitory media and non-transitory media. Transitory media include transmission media (e.g., metal cables, fiber optics), signals, carrier waves, and the like. Non-transitory media include magnetic media (e.g., disks and tapes), optical media (e.g., CD ROM, digital video disks, Blu-ray disks), solid-state media (e.g., RAM, ROM, flash memory, solid-state storage), and other non-volatile storage or memory.

Computer device 1705 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C#, Java, Visual Basic, Python, Perl, JavaScript, and others).

Processor(s) 1710 can execute under any operating system (OS) (not shown), in a native or virtual environment. One or more applications can be deployed that include logic unit 1760, application programming interface (API) unit 1765, input unit 1770, output unit 1775, and inter-unit communication mechanism 1795 for the different units to communicate with each other, with the OS, and with other applications (not shown). The described units and elements can be varied in design, function, configuration, or implementation and are not limited to the descriptions provided. Processor(s) 1710 can be in the form of hardware processors such as central processing units (CPUs) or in a combination of hardware and software units.

In some example implementations, when information or an execution instruction is received by API unit 1765, it may be communicated to one or more other units (e.g., logic unit 1760, input unit 1770, output unit 1775). In some instances, logic unit 1760 may be configured to control the information flow among the units and direct the services provided by API unit 1765, the input unit 1770, the output unit 1775, in some example implementations described above. For example, the flow of one or more processes or implementations may be controlled by logic unit 1760 alone or in conjunction with API unit 1765. The input unit 1770 may be configured to obtain input for the calculations described in the example implementations, and the output unit 1775 may be configured to provide an output based on the calculations described in example implementations.

Processor(s) 1710 can be configured to receive, via a wireless communication device and from a wireless device of the taVNS system, configuration information for configuring the provision of adjustable electrical pulses. The processor(s) 1710 can be configured to provide, based on the configuration information, the adjustable electrical pulses via the earclip. The processor(s) 1710 can be configured to execute an application used to specify the configuration information and is further configured to provide the configuration information to the wireless communication device of the powersource. The processor(s) 1710 can be configured to communicate with a wireless communication device via Bluetooth. The processor(s) 1710 can be configured to determine whether the earclip is connected to a user while providing the configurable electrical pulses. The processor(s) 1710 can be configured to transmit monitoring information regarding whether the earclip is connected to the user to the wireless device. The processor(s) 1710 can also be configured to provide, based on the monitoring information, additional monitoring information to a remote monitoring system.

Some portions of the detailed description are presented in terms of algorithms and symbolic representations of operations within a computer. These algorithmic descriptions and symbolic representations are the means used by those skilled in the data processing arts to convey the essence of their innovations to others skilled in the art. An algorithm is a series of defined steps leading to a desired end state or result. In example implementations, the steps carried out require physical manipulations of tangible quantities for achieving a tangible result.

Unless specifically stated otherwise, as apparent from the discussion, it is appreciated that throughout the description, discussions utilizing terms such as "processing," "computing," "calculating," "determining," "displaying," or the like, can include the actions and processes of a computer system or other information processing device that manipulates and transforms data represented as physical (electronic) quantities within the computer system's registers and memories into other data similarly represented as physical quantities within the computer system's memories or registers or other information storage, transmission or display devices.

Example implementations may also relate to an apparatus for performing the operations herein. This apparatus may be specially constructed for the required purposes, or it may include one or more general-purpose computers selectively activated or reconfigured by one or more computer programs. Such computer programs may be stored in a computer readable medium, such as a computer readable storage medium or a computer readable signal medium. A computer readable storage medium may involve tangible mediums such as, but not limited to optical disks, magnetic disks, read-only memories, random access memories, solid-state devices, and drives, or any other types of tangible or non-transitory media suitable for storing electronic information. A computer readable signal medium may include mediums such as carrier waves. The algorithms and displays presented herein are not inherently related to any particular computer or other apparatus. Computer programs can involve pure software implementations that involve instructions that perform the operations of the desired implementation.

Various general-purpose systems may be used with programs and modules in accordance with the examples herein, or it may prove convenient to construct a more specialized apparatus to perform desired method steps. In addition, the example implementations are not described with reference to any particular programming language. It will be appreciated that a variety of programming languages may be used to implement the teachings of the example implementations as described herein. The instructions of the programming language(s) may be executed by one or more processing devices, e.g., central processing units (CPUs), processors, or controllers.

As is known in the art, the operations described above can be performed by hardware, software, or some combination of software and hardware. Various aspects of the example implementations may be implemented using circuits and logic devices (hardware), while other aspects may be implemented using instructions stored on a machine-readable medium (software), which if executed by a processor, would cause the processor to perform a method to carry out implementations of the present application. Further, some example implementations of the present application may be performed solely in hardware, whereas other example implementations may be performed solely in software. Moreover, the various functions described can be performed in a single unit, or can be spread across a number of components in any number of ways. When performed by software, the methods may be executed by a processor, such as a general-purpose computer, based on instructions stored on a computer readable medium. If desired, the instructions can be stored on the medium in a compressed and/or encrypted format.

Moreover, other implementations of the present application will be apparent to those skilled in the art from consideration of the specification and practice of the teachings of the present application. Various aspects and/or components of the described example implementations may be used singly or in any combination. It is intended that the specification and example implementations be considered as examples only, with the true scope and spirit of the present application being indicated by the following claims.

EXAMPLES

Example 1—VNS Intervention Trial for Autistic Children Patient Population

A total of 885 children who presented for care of autism and developmental disorders were first interviewed by a physician with expertise in treatment and clinical management of autism and developmental disorders. The interview reviewed neurological domains to assess the present status of neurological delay in these domains. The domains included eye contact, awareness, focus and attention, receptive language, expressive language, emotional regulation, hyperactivity, anxiety, sleep patterns, and intestinal function (diarrhea vs. constipation).

The physician recorded features in each of these areas, especially in the context of the child's developmental stage, immediately before initiation of therapy. Examples of the developmental process for some of these neurological domains are displayed in graphics 1-6. Each domain was given a 7-level scale ranging from greatest severity of symptoms to lowest severity of symptoms. For example, in the "socialization" domain, the greatest severity was "does not interact with anyone," followed by "interacts with mother (primary caregiver)." The second-lowest severity was "interacts with unfamiliar children" and the lowest severity was "appropriately socializes with peers." These assessments were used to give the managing physician a baseline against which to compare any prior gains or regressions that may occur over time with or without treatment. For example, with treatment a child might progress from "does not interact with anyone" to "interacts with mother (primary caregiver)," or might remain at "does not interact with anyone."

After the interview process was complete, each child was placed on a treatment protocol that utilized two essential components: (1) stabilization of omega-3 and omega-6 fatty acids with daily consumption of fish oil and olive oil, and (2) reversal of underlying small intestine bacteria overgrowth (SIBO) with either daily consumption of prebiotic fiber (inulin), twice-daily dosing with rifaximin (a non-absorbable antibiotic), or a combination of both.

Parents were instructed to look for signs of neurological improvement expected to occur within a few weeks of initiating the above therapy. The physician interviewed the parents every four months using the same criteria as in the initial interview, and parents were asked whether the neurological domains had improved, stayed the same, or worsened. Detailed notes were also taken. The parents were asked to report the neurological status as a collective input from their own observations and input from teachers, school aides, and trained ABA, speech, physical and occupational therapists involved in the child's care. After 4-8 months, the interviewed parents described dramatic increases in the pace of neurological recovery in many developmental domains compared to the initial baseline assessment. When neurological improvements were observed across all domains, the treatment regimen was not altered.

In 538 of the 885 patients, the interviews revealed that although there were improvements in some domains, one or more domains had no improvement. For these refractory patients, once-daily transcutaneous vagus nerve stimulation (tVNS) was prescribed.

VNS Treatment

In the 538 refractory patients, transcutaneous VNS was applied to the concha of either ear using 5 Hz, 500 μs and 10 v current over a 5 minute stimulation period, once daily. Parents were interviewed every four months after the initiation of VNS as described above.

Results

Parents often reported that whatever domain was not recovering finally demonstrated significant neurological gains within a few weeks of initiating VNS.

Among the 538 treated patients, 256 were simultaneously treated with other changes to the basal treatment regimen and were thus not included in the VNS analysis because of the presence of potentially confounding factors.

Among the remaining 282 treated, analyzed children, 238 (i.e., 84.4%) showed improvement in one or more domains that were previously not showing any improvement. These domains were Speech, Comprehension, Socialization, Aggression, and Focus & Attention. The improvements in each domain were as follows:

Total: 84.4% showed improvement (238 out of 282 children)

Speech: 83.9% showed improvement (115 out of 137 children previously showing no speech improvement)

Comprehension: 85.4% showed improvement (35 out of 41 children previously showing no comprehension improvement)

Socialization: 83.3% showed improvement (30 out of 36 children previously showing no socialization improvement)

Aggression: 90.4% showed improvement (47 out of 52 children previously showing no aggression improvement)

Focus & Attention: 90.3% showed improvement (56 out of 62 children previously showing no focus & attention improvement)

The results represent a stark improvement from the baseline in the vast majority of patients treated, even though these patients were refractory to the first-line treatment provided (which itself was effective in 39% of the full patient population).

What is claimed is:

1. A method for preventing, treating, or preventing recurrence of symptoms of autism or autism spectrum disorder in a subject in need thereof, said method comprising:
   administering to said subject electrical transcutaneous auricular vagus nerve stimulation (taVNS) applied to the tragus or concha of an ear with a frequency of 2-5 Hz, pulse width of 150-500 μs, and current of 0.5-1.0 mAmps, wherein symptoms of autism or autism spectrum disorder are prevented, treated, or prevented from recurring, wherein the subject is a child who is refractory to standard autism treatments.

2. The method of claim 1, wherein the subject exhibits inflammation or gut microbiome dysfunction.

3. The method of claim 1, wherein the VNS is provided transcutaneously using electrical stimulation through an electrical current.

4. The method of claim 3, wherein the electrical stimulation is achieved by clipping electrodes across the tragus or concha of an ear and inducing an electrical current with a transcutaneous electrical nerve stimulation (TENS) unit.

5. The method of claim 3, wherein the electrical stimulation is performed for about 30 sec to about 10 min.

6. The method of claim 5, wherein the number of doses per day is selected from the group consisting of 1, 2, 3, 4, 5, 6, 7, 8, 9, 10, 11, 12, 13, 14, 15, 16, 17, 18, 19, 20.

7. The method of claim 5, wherein the length of treatment is 1 to 120 months.

8. The method of claim 5, wherein the subject receives 1-2, 5-minute treatments per day for 48 months.

* * * * *